(12) United States Patent
Makower et al.

(10) Patent No.: US 7,159,592 B1
(45) Date of Patent: Jan. 9, 2007

(54) METHODS AND APPARATUS FOR TRANSMYOCARDIAL DIRECT CORONARY REVASCULARIZATION

(75) Inventors: Joshua Makower, Los Altos, CA (US); J. Christopher Flaherty, Los Altos, CA (US); Timothy R. Machold, Moss Beach, CA (US); Jason Brian Whitt, San Francisco, CA (US); Margaret W. Tumas, Orinda, CA (US); Theodore C. Lamson, Pleasanton, CA (US); Marc Jensen, Los Gatos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 451 days.

(21) Appl. No.: 09/710,332

(22) Filed: Nov. 9, 2000

Related U.S. Application Data

(63) Continuation of application No. 09/059,531, filed on Apr. 13, 1998, now abandoned, which is a continuation-in-part of application No. 08/837,295, filed on Apr. 11, 1997, now abandoned, which is a continuation-in-part of application No. 08/730,496, filed on Oct. 11, 1996, now Pat. No. 5,830,222, which is a continuation-in-part of application No. 08/730,327, filed on Oct. 11, 1996, now Pat. No. 6,190,353.

(60) Provisional application No. 60/028,922, filed on Aug. 26, 1996, provisional application No. 60/005,164, filed on Oct. 13, 1995.

(51) Int. Cl.
*A61B 19/00* (2006.01)

(52) U.S. Cl. .................................. 128/898; 606/108
(58) Field of Classification Search ............... 128/898; 604/49, 96, 7, 8, 9; 606/194, 1, 108, 167, 606/170, 171; 623/1.1, 1.11
See application file for complete search history.

(56) References Cited

U.S. PATENT DOCUMENTS

| 4,865,581 | A  | * | 9/1989 | Lundquist et al. ............ 600/18 |
| 5,533,957 | A  | * | 7/1996 | Aldea ........................... 600/16 |
| 5,655,548 | A  | * | 8/1997 | Nelson et al. ............... 128/898 |
| 6,447,539 | B1 | * | 9/2002 | Nelson et al. ............. 623/1.11 |

* cited by examiner

*Primary Examiner*—David J. Isabella

(57) ABSTRACT

Methods and apparatus for direct coronary revascularization wherein a transmyocardial passageway is formed between a chamber of the heart and a coronary blood vessel to permit blood to flow therebetween. In some embodiments, the transmyocardial passageway is formed between a chamber of the heart and a coronary vein. The invention includes unstented transmyocardial passageways, as well as transmyocardial passageways wherein protrusive stent devices extend from the transmyocardial passageway into an adjacent coronary vessel or chamber of the heart. The apparatus of the present invention include protrusive stent devices for stenting of transmyocardial passageways, intraluminal valving devices for valving of transmyocardial passageways, intracardiac valving devices for valving of transmyocardial passageways, endogenous tissue valves for valving of transmyocardial passageways, and ancillary apparatus for use in conjunction therewith.

34 Claims, 14 Drawing Sheets

METHODS AND APPARATUS FOR TRANSMYOCARDIAL DIRECT CORONARY REVASCULARIZATION

RELATED APPLICATIONS

This application is a continuation of application Ser. No. 09/059,531, filed Apr. 13, 1998, Abn which is a continuation-in-part of three parent applications, namely application Ser. No. 08/730,327, filed Oct. 11, 1996, now U.S. Pat. No. 6,190,353, application Ser. No. 08/730,496, filed Oct. 11, 1996, now U.S. Pat. No. 5,830,222, both of which claim priority to Provisional Application No. 60/005,164 filed Oct. 13, 1995 and application Ser. No. 08/837,295, filed Apr. 11, 1997, Abn which claims priority to Provisional Application No. 60/028,922, filed Aug. 26, 1996, and also is a continuation-in-part of application Ser. No. 09/730,327, filed Oct. 11, 1996, now U.S. Pat. No. 6,190,353 and application Ser. No. 09/730,496, filed Oct. 11, 1996, now U.S. Pat. No. 5,830,222. The entire disclosures of such related applications are incorporated herein by reference herein.

FIELD OF THE INVENTION

The present invention pertains generally to medical treatment methods and devices, and more particularly to methods and devices for transluminal direct coronary revascularization.

BACKGROUND OF THE INVENTION i. Coronary Artery Disease

Coronary artery disease continues to be one of the leading causes of morbidity and mortality, throughout the world. The typical etiology of coronary artery disease is characterized by the build-up of atherosclerotic plaque within the coronary arteries. Such deposits of atherosclerotic plaque tend to fully or partially block the flow of blood through the affected coronary arteries, and if untreated can result in myocardial ischemia, infarction and death.

For many years, the traditional surgical treatment of coronary artery disease has been coronary artery bypass surgery. In traditional coronary artery bypass surgery, the patient is generally anesthetized and placed on cardiopulmonary bypass. A thoracotomy is performed and the obstructed coronary blood vessels are exposed by surgical dissection. One or more segments of the patient's saphenous vein or internal mammary artery is/are harvested for use as bypass graft(s). The harvested segment(s) of vein or artery is/are then anastomosed to the obstructed coronary artery (ies) to form bypass conduit(s) around the arterial obstruction(s). Such traditional coronary artery bypass surgery is expensive, extremely invasive, and is associated with significant operative and perioperative complications.

One alternative to traditional coronary artery bypass surgery is balloon angioplasty. In balloon angioplasty, a flexible guide catheter is percutaneously inserted into a peripheral artery (e.g., the femoral artery) and is transluminally advanced through the vasculature until the distal tip of the catheter is within an obstructed coronary artery. Thereafter, a balloon catheter is passed through the guide catheter and into the obstructive lesion. The balloon of the balloon catheter is inflated one or more times to dilate coronary artery in the region of the obstructive lesion. These balloon angioplasty procedures tend to be less expensive and less traumatic than traditional coronary artery bypass surgery. However, balloon angioplasty procedures of this type have been associated with a significant incidence of restenosis at the angioplasty site. The cause and mechanism of such restenosis continues to be the subject of ongoing study. However, such restenosis has generally been attributed to either a) an increase in the mass of the artery wall (e.g., neointima formation), b) a thickening of the artery wall without substantial change in it's mass (e.g., vascular remodeling) and/or c) radial contraction of the balloon-dilated artery wall upon healing of cracks and fissures that have been created by the balloon dilation process.

Another alternative to traditional coronary artery bypass surgery is transluminal atherectomy or ablation of the obstructive matter within the coronary artery. These transluminal atherectomy or ablation procedures are performed by passing a catheter-mounted ablation apparatus through the vasculature to the site of the coronary obstruction the catheter-mounted ablative apparatus is then utilized to cut, shave, sonicate, pulverize or otherwise ablate the obstructive matter from the lumen of the coronary artery. These atherectomy or ablative procedures must be performed with caution to avoid abrasion or damage to the artery wall, as such abrasion or damage can result in excessive scaring and subsequent reclusion of the artery lumen. Furthermore, these atherectomy or ablative procedures may, in some cases at least, be confounded by the need to meticulously contain and remove the severed fragments of obstructive matter in order to prevent such fragments of obstructive matter from escaping into the patient's circulatory system. Examples of such atherectomy catheters and other catheter-mounted ablative apparatus are described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), 4B70,953 (Don Michael, et al.), U.S. Pat. No. 5,069,664 (Suess, et al.), U.S. Pat. No. 4,920,954 (Alliger, et al.) and U.S. Pat. No. 5,100,423 (Fearnot), as well as foreign patents/patent publications EP0347098A2 (Shiber), WO87-05739 (Cooper), WO89-06515 (Bernstein, et al.), WO90-0130 (Sonic Needle Corp.), EP316789 (Don Michael, et al.), DE 3,821,836 (Schubert), DE2438648 (Pohlman), and EP 0443256A1 (Baruch).

Other alternatives to traditional coronary artery bypass surgery have included minimally invasive endoscopic procedures which, ostensibly at least, can be performed through small (e.g., 1–3 cm) incisions formed in the patient's chest wall, by insertion of a thoracoscope and associated operative instruments through such incisions. One such thoracoscopic coronary bypass procedure is described in U.S. Pat. No. 5,452,733 (Sterman et al.). If perfected, these minimally invasive coronary artery bypass procedures may lessen the discomfort and length of recovery time experienced by patients who undergo such minimally invasive procedures vis a vis those who undergo traditional coronary artery bypass surgery. However, the performance of endoscopic surgical procedures of this type typically requires a great deal of operator skill and training. Furthermore, as with traditional coronary artery bypass surgery, the patients on whom these thoracoscopic procedures are performed are likely to undergo general anesthesia (with or without cardiopulmonary bypass) and the creation of a pneumothorax due to the formation of full-thickness incision(s) in the chest wall. Thus, many of the drawbacks associated with traditional coronary artery bypass surgery, are also associated with these minimally invasive thoracoscopic procedures.

ii. Transmyocardial Revascularization

Another type of procedure which has been devised for improving blood flow to ischemic regions of the myocardium is known as transmyocardial revascularization (TMR). These TMR procedures generally involve the formation of tunnels or passageways through the myocardial muscle for the purpose of providing improved blood flow. In one such TMR procedure, a tissue-boring device, such as a laser, is utilized to form a series of small-diameter passageways from the epicardial surface of the heart, through the myocardium, and into the left ventricle. Jeevanandam, et al., *Myocardial Revascularization By Laser-Induced Channels*, Surgical Forum XLI, 225–227 (October 1990); also see, U.S. Pat. No. 4,658,817 (Hardy).

A variant of the above-described TMR procedure is described in U.S. Pat. No. 5,389,096, (Aita, et al.), wherein a catheter-mounted tissue-boring apparatus (e.g., a laser) is advanced into a chamber (i.e., left ventricle) of the heart and is used to form a plurality of blind, partial-thickness passageways from the chamber of the heart into the myocardium.

Modified TMR procedures have also been described wherein an internally valved transmyocardial passageway is formed between a coronary artery and the left ventricle of the heart, such that blood from left ventricle may flow into the coronary artery. These modified TMR procedures, hereinafter generally referred to as "Transmyocardial Direct Coronary Revascularization" (TMDCR), are described in U.S. Pat. No. 5,287,861 (Wilk), U.S. Pat. No. 5,409,019 (Wilk), and U.S. Pat. No. 5,429,114 (Wilk). At least some of these TMDCR methods require that a catheter be introduced into the obstructed coronary artery and advanced through the obstructive lesion. After the catheter has been advanced through the obstructive lesion, the distal tip of the catheter is stirred or bent toward the artery wall and a tissue-penetrating element is passed through the artery wall, through the adjacent myocardium, and into the chamber of the left ventricle. Also, in this previously described TMDCR method, a stent or valving apparatus is required to be positioned within the transmyocardial passageway to perform a one-way valving function (i.e., to open and close the transmyocardial passageway in accordance with changes in the systolic-diastolic cardiac cycle).

These TMDCR methods, previously described in U.S. Pat. No. 5,287,861 (Wilk), U.S. Pat. No. 5,409,019 (Wilk) and U.S. Pat. No. 5,429,114 (Wilk), may be difficult or impossible to perform in patients who suffer from total or near total obstructions of a coronary artery, because of the necessary for advancing the catheter through the coronary artery obstruction to accomplish creation of the transmyocardial passageway at a location which is downstream of the coronary obstruction. Furthermore, because these previously described TMDCR methods require placement of a stent within the transmyocardial passageway, such procedures are necessarily associated with procedural complexities associated with measuring and pre-cutting the stent to a precise length so that it fits within the transmyocardial passageway without protruding into the chamber of the left ventricle and/or the lumen of the coronary artery. Also, any stent which is positioned solely within the transmyocardial passageway may be subject to repetitive flexing and/or stressing as the myocardium undergoes its normal contraction and relaxation. Such repeated flexing and/or stressing of the intramyocardial stent may lead to unwanted migration, dislodgement or damage of the stent.

iii. Intermittent Coronary Sinus Occlusion For Coronary Retroperfusion

Yet another procedure which has been proposed as a means for treating acute myocardial ischemia is known as intermittent coronary sinus occlusion (ICSO). In many if not all ICSO procedures, the inflatable balloon is placed in the coronary sinus and is attached to a mechanical pump. The mechanical pump operates to intermittently inflate and deflate the balloon so as to intermittently occlude the coronary sinus. Such intermittent inflation and deflation of the balloon may be linked to the coronary sinus pressure so as to optimize the retroperfusion of the ischemic myocardium. Specific ICSO procedures have been described in Belamy, R. F: (et al.) *Effect of Coronary Sinus Occlusion on Coronary Pressure-Flow Relations*, Am. J. Physiol. 239 (Heart Circ. Physiol. 8) HS 57-HS64, 1980; Pantely, G. A. (et al.) *Effect of Resistance, And Zero Flow Pressure During Maximum Vasodilation in Swine*, Cardiovascular Research, 22:79–86, 1988.

Because the coronary sinus balloon is typically mounted on a percutaneously inserted catheter and is connected to an extracorporeally located pumping system, the clinical usefulness of these ICSO procedures is presently limited to temporary applications intended to minimize heart muscle damage following infarction or during acute periods of myocardial ischemia. However, the general concept of these ICSO procedures could be applicable for the long-term treatment of chronic myocardial ischemia if a totally indwelling system could be devised which would eliminate the need for continued coronary sinus catheterization and/or the deployment of an extracorporeal pumping apparatus connected to such catheter.

When considering the manner in which the ICSO procedures operate, it is helpful to bear in mind that the human circulatory system functions to send oxygenated blood from the aorta to the heart muscle (myocardium) via the left and right coronary arteries (small and large arteries). Following the oxygen/metabolite exchange in the myocardium, the venous system returns the de-oxygenated blood via the epicardial veins (large and small veins). A small fraction of the de-oxygenated blood returns through a set of small vessels which empty directly into the chambers of the heart called the Thebesian veins. Support exists in clinical literature that these Thebesian vessels can carry as much as 90 percent of the total coronary inflow back into the chambers of the heart. The Thebesian vessels connect to both the venous and arterial beds in an interface at the capillary level. Based upon this knowledge of heart function, researchers have suggested that occluding the venous system (e.g. blocking the coronary sinus or other large vein), does not compromise heart function and may in fact create a beneficial effect in cases of diseased or ischemic myocardium.

One particular type of ICSO procedure, known as pressure-controlled intermittent coronary sinus occlusion (PICSO), and apparatus for performing such procedure are described in European Patent Application No. EP0230996 to Mohl. In this PICSO procedure, an external balloon catheter is inflated in the coronary sinus for a period of time (several cardiac cycles). This PICSO procedure is typically performed in a hospital setting, during a coronary catheterization procedure. This PICSO procedure has been shown to elevate the pressure in the venous bed, providing a therapeutic benefit. (see, Mohl, *The Development and Rationale of Pressure Controlled Intermittent Coronary Sinus Occlusion-A New Approach to Protect Ischemic Myocardium*, Wiener klinische Wochenschrift, pp 20–25, Jan. 6, 1984; also see, Moser, *Optimization of Pressure Controlled Inter-* mittent Coronary Sinus Occlusion Intervals by Density Measurements, in *The Coronary Sinus*, Eds. Mohl, Wolner, Glogar, Darmstadt: Steinkopff Verlag, 1984 pp. 529–536; Schreiner, *The Role of Intramyocardial Pressure During Coronary Sinus Interventions: A Computer Model Study*, IEEE Transactions on Biomedical Engineering, Vol. 37, No. 10, October (1990). In addition, research has shown that, in patients who suffer from occlusive coronary artery disease, venous occlusion may actually prevent or reduce the size of a subsequent infarct (heart attack). (Kralios, *Protective Effect of Coronary Sinus Obstruction from Primary Ischemia-Induced Ventricular Fibrillation in the Dog*, Am. Heart J (1993) 125:987; Lazar, *Reduction of Infarct Size With Coronary Venous Retroperfusion*, Circulation (1992) 86:II 352).

There currently exists a need to provide minimally invasive methods and devices which have the capability of achieving therapeutic effects similar to those of the above-described PICSO procedure of the prior art, but which do not require continuing cardiac catheterization of the patient in order for the beneficial effects of the procedure to remain. Accordingly, it is the object of the present invention to describe various devices that can be implanted percutaneously in the patient's coronary sinus or great cardiac vein where they remain implanted to achieve partial or total occlusion of the coronary venous system. One mechanism of the therapeutic benefits seen clinically are understood to be based upon the slowing of the arterial flow and subsequently the increased the dwell time of the blood in the capillary bed allowing for an increased oxygen-metabolite exchange. The benefits of this phenomenon are better oxygen uptake and potentially a decrease in the infarct size in the event of a future cardiac arrest, and/or potentially global ischemic protection. Another mechanism providing potential benefit is the resultant redistribution of flow through collateral capillary beds, allowing perfusion of regions of the heart that may be otherwise ischemic (lack of perfusion of blood flow due to disease in vessels feeding those regions). In addition, angiogenesis, a stimulation of the endothelial cells lining the internal walls of vessels to form new blood vessels, may be stimulated as a compensatory mechanism in response to the disruption of normal venous blood flow, thereby providing additional myocardial perfusion through newly created blood flow conduits.

In view of the above-summarized shortcomings and complexities of the previously described TMDCR methods, there exists a need in the art for the development of improved TMDCR methods and associated apparatus which may be utilized without the need for cumbersome stenting of the transmyocardial passageway and/or implantation of one-way valving apparatus within the transmyocardial passageway. Also, there exists a need for the development of a new TMDCR methods which can be performed in patients who suffer from total or near total coronary artery occlusion(s), without the need for advancing a catheter through such coronary artery occlusion(s).

SUMMARY OF THE INVENTION

The present invention provides new TMDCR methods, as well as certain valving devices which are usable in conjunction with these TMDCR methods.

i. TMDCR Procedures Wherein Transmyocardial Passageway Is Formed Between a Chamber of the Heart and a Coronary Vein In accordance with the present invention, there is provided a specific TMDCR method wherein a transmyocardial passageway is formed between a chamber of the heart (e.g., left ventricle) and a coronary vein. In this embodiment of the invention, blood may pass from the cardiac chamber, through the transmyocardial passageway, and into the coronary vein for the purpose of improving blood flow to the myocardium and/or to equalize or normalize pressures within the coronary venous vasculature by draining blood from the vein into the cardiac chamber. The coronary vein of this embodiment may be situated next to an obstructed coronary artery, and one or more secondary blood flow passageways may be created between the coronary vein and the adjacent artery, at site(s) which is/are downstream of the coronary artery obstruction. Also, the lumen(s) of the coronary vein and/or adjacent coronary artery may be blocked or embolized at appropriate positions to facilitate the flow of blood in the desired direction(s) through the man-made blood flow passageway(s), the coronary vein and/or the coronary artery. Additionally, one or more valving apparatus may be positioned within the coronary vein and/or within the cardiac chamber, to control or intermittently block the flow of blood through the transmyocardial passageway.

ii. TMDCR Procedures Wherein Temporary A-V Fistula is Used to Facilitate Formation of Transmyocardial Passageway Entering Coronary Artery Downstream of Obstruction or Other Intravascular Procedure Further in accordance with the present invention, there are provided TMDCR procedures wherein a transmyocardial passageway-forming catheter is initially advanced into a coronary vein which lies adjacent to an obstructed coronary artery. The passageway forming catheter is advanced through the coronary vein until the distal end of the catheter is adjacent a location on the coronary artery which is downstream of the coronary artery obstruction. Thereafter, the passageway-forming catheter is utilized to form an arterio-venous passageway which extends from the coronary vein wherein the catheter is located into the coronary artery, at a site downstream of the obstruction. Thereafter, the passageway-forming catheter is advanced through the arterio-venous passageway and into the coronary artery. The passageway-forming catheter is then oriented such that the tissue-penetrating element of the catheter will pass out of the catheter, through the wall of the artery and into a chamber of the heart (e.g., left ventricle). Thereafter, the tissue-penetrating catheter is removed and the arterio-venous passageway, which had been initially formed to allow the passageway-forming catheter to enter the coronary artery downstream of the obstruction, is closed by way of an occlusion apparatus, sutures, cautery, adhesive, or any other suitable tissue closure method or apparatus. Thus, by this procedure, a transmyocardial passageway is formed between a chamber of the heart (e.g., left ventricle) and an obstructed coronary artery, at a site downstream of the coronary artery obstruction, without the need for advancing any guidewire, catheter or other apparatus through the obstruction located within the coronary artery.

The temporary arteriovenous fistula created in this procedure may also be used for other purposes, such as to perform an atherectomy within the lumen of the occluded vessel, or to place a guidance/aiming apparatus (e.g., a target or signal-emitting apparatus) within the lumen of the occluded artery downstream of the obstruction to facilitate formation of a transmyocardial or interstitial passageway into the occluded blood vessel, downstream of the obstruction. This aspect of the invention will be particularly useful in patients in whom the obstruction is sufficiently complete as to prevent a catheter from being passed through the obstruction, but in whom it is desirable to catheterize the distal portion of the occluded blood vessel downstream of the obstruction to accomplish a therapeutic procedure (e.g., atherectomy, ablation of the occlusive matter, placement of a target, etc.)

iii. Other Procedures Using The Temporary A-V Fistula

Further in accordance with the invention, a temporary arterio-venous fistula of the above-described type may be utilized to facilitate the performance of other therapeutic or interventional procedures within the lumen of a blood vessel, downstream of an occlusion. This aspect of the invention will be particularly applicable in patients who have total or near total occlusions of an artery, and in whom it would be difficult or impossible to advance a catheter through the total or near total occlusion.

The types of interventional or therapeutic procedures which may be performed through the temporary arterio-venous fistula include, but ar not necessarily limited to, balloon angioplasty, atherectomy, stenting, thrombolysis, full or partial ablation or removal of occlusive matter, or installation of an apparatus (e.g., a signal-emitting target) into the lumen of the blood vessel, downstream of the obstruction.

This aspect of the invention may be particularly useful in patients who have previously undergone coronary artery bypass surgery such that a bypass graft is anastomosis to a coronary artery, downstream of a total or near total obstruction. In those patients, it is not unusual for a secondary obstruction to form immediately downstream of the anastomosis of the bypass graft. In the event that such secondary obstruction does form, the temporary arterio-venous fistula of the present invention may be used to permit an interventional apparatus (e.g., balloon angioplasty catheter, thrombolysis catheter, atherectomy catheter, ablation catheter, stent-delivery catheter, etc.) into the lumen of the coronary artery, downstream of the obstruction, to treat the secondary obstruction which has formed adjacent the anastomosis. After such therapeutic or interventional procedure has been completed, the temporary arterio-venous fistula may be closed by the above-described procedure, thereby restoring pathency to the segment of the artery downstream of the bypass graft anastomosis.

iv. TMDCR Procedures Using Unstented Transmyocardial Passageway

Further in accordance with the present invention, there is provided a method for coronary re-vascularization wherein an unstented transmyocardial passageway (e.g., a puncture tract, bore, tunnel, or other passageway) is formed between a chamber of the heart (e.g., the left ventricle) and a coronary vessel (e.g., a) an endogenous coronary artery; b) an endogenous coronary vein; c) a man-made passageway which has been formed in the heart, and which leads to an endogenous coronary vein; d) a man-made passageway which has been formed in the heart, and which leads to an endogenous coronary artery; and/or e) a man-made passageway which has been formed in the heart between an endogenous coronary artery and an endogenous coronary vein). The unstented transmyocardial passageway(s) created in accordance with this embodiment of the invention may be utilized to improve perfusion of the myocardium by shunting blood from the chamber of the heart (e.g., left ventricle) into the coronary vessel (e.g., vein artery or man-made passageway), or may alternatively be utilized to equalize or normalize flow or pressure within the cardiac vasculature by draining blood from one or more cardiac vessels (e.g., vein, artery or man-made passageway), into the chamber of the heart.

v. Valving Devices Positionable in Coronary Vessels

Still further in accordance with the present invention, there are provided several types of intraluminal valving apparatus which may be positioned within the lumen(s) of the coronary blood vessel(s) (i.e., artery, vein or man-made passageway) which intersect with the transmyocardial passageway, to intermittently block bloodflow, in at least one direction, through the transmyocardial passageway. These intraluminal valving devices generally comprise tubular bodies having at least one occluder member positioned therein, said occluder member(s) being alternately moveable between i) open position(s) whereby bloodflow is permitted to pass through the transmyocardial bloodflow passageway in a desired direction, and ii) closed position(s) whereby blood is prevented from flowing through the transmyocardial bloodflow passageway, in an undesired direction.

vi. Tissue Valves For TMDCR Passageway

Alternatively, the present invention also includes endogenous tissue valve(s) which are formed in the transmyocardial passageway to perform a desired one-way valving function whereby blood is permitted to flow through the transmyocardial bloodflow passageway in a first direction, but is prevented from backflowing or regurgitating in a second direction.

vii. Intracardiac Valving Devices For TMDCR Passageway

Still further in accordance with the present invention, there are provided intracardiac valving devices which are mountable within a chamber of the heart (e.g., left ventricle) immediately adjacent to an opening into a transmyocardial passageway which extends from the cardiac chamber to a coronary vessel (e.g., artery, vein or man-made passageway). Such intracardiac valving device may be constructed such that it will open in response to hemodynamic pressure generated during systole and/or in response to mechanical contraction (i.e., shortening and thickening) of the myocardium during systole. When open, the intracardiac valving device permits blood to flow through the transmyocardial bloodflow passageway. Thereafter, the valving device may be constructed to close when diastolic pressures are present in the cardiac chamber or when the myocardium undergoes mechanical relaxation (i.e., lengthening and thinning during diastole. When closed, the valving device will prevent blood from backflowing or regurgitating from the transmyocardial bloodflow passageway, into the cardiac chamber.

viii. Protrusive Stents and Stented Grafts For TMDCR Passageways

Still further in accordance with the present invention, there are provided stents and stented grafts which are positionable within the transmyocardial passageway, and which protrude into the adjacent coronary vessel (e.g., vein, artery or man-made passageway). These protrusive stents and/or protrusive stented grafts may be self-expanding or pressure-expandable. Optionally, one or more valves or occluder members may be positioned within such protrusive stents and/or stented grafts to facilitate valving or directed movement of bloodflow in accordance with the diastolic/systolic cardiac cycle.

ix. Intravascular Valving Apparatus and Methods for Intermittent Coronary Venous Occlusion Still further in accordance with the present invention, there are provided intravascular valving devices which are positionable within the coronary sinus, great cardiac vein or other areas of the coronary venous vasculature to control the back pressure within one or more coronary veins in a manner which will result in increased dwell time of the arterial blood within the capillary bed of the ischemic myocardium, and/or dilation of the capillary bed, thereby improving perfusion of the ischemic region(s) of the myocardium.

These intravascular valving devices may generally comprise a radially expandable cylindrical frame having one or more leaflets or other occluding members (e.g., ball-in-cage type check valve, etc.) which are specifically configured and constructed to prevent venous outflow until the pressure within the coronary sinus, great cardiac vein or other coronary vein exceeds a predetermined amount. Optionally, one or more transmyocardial passageways may be formed between the coronary vein(s) and/or coronary artery(s) to provide additional blood flow into the coronary vasculature in conjunction with the increased back pressure created by this intravascular valving apparatus. Alternatively or additionally, these intravascular valving apparatus of the present invention may be implanted within the coronary sinus, great cardiac vein, or other coronary vein to regulate coronary venus pressure in conjunction with an interstitial arteriovenous passageway or passageway formed between a chamber of the heart and a coronary vein, in accordance with the procedures previously described in applicant's U.S. patent application Ser. Nos. 08/730,327 and 08/730,496, filed on Oct. 11, 1996. The tissue penetrating member will reside when varying lengths of said tissue penetrating member have been advanced out of the catheter, said imaging means being thereby useable to focus on a selected one of said distance indicia to optimally position the catheter to form the desired passageway.

Optionally, these intravascular valving apparatus may incorporate one or more of the following additional features:

The valving apparatus may be pucturable or traversable so as to permit a catheter to be passed through the valving apparatus in the event that such catheter passage becomes necessary at a later time;

The valving apparatus may be removable such that it may be rescued and removed from the body in the event it is no longer necessary, or if removal becomes desirable for some other reason;

The valving apparatus may be provided with projections, hooks, material for tissue in growth, or other suitable anchoring apparatus to assist in holding the valving apparatus in its desired position within the venus lumen; and The valving apparatus may be formed of radiologically imagable material, or may be provided with one or more radio dense or radio opaque markers to facilitate visualization of the valving apparatus by x-ray or fluoroscopy.

These intravascular valving apparatus of the present invention are implantable within the coronary sinus, great cardiac vein or other coronary vein, and will remain indwelling so as to regulate back pressure within the system and/or to improve myocardial perfusion, on an ongoing basis, without the need for continued placement of a catheter-mounted counterpulsation balloon within the coronary sinus and/or deployment of any extracorporeal instrumentation, such as the extracorporeal pumping apparatus which has been traditionally required for intermittent inflation and deflation of the coronary sinus counterpulsation balloon.

Further objects and advantages of the present invention will become apparent to those skilled in the art upon reading and understanding of the following detailed descriptions of preferred embodiments.

BRIEF DESCRIPTION OF THE DRAWINGS

FIG. 8b is a longitudinal sectional view showing an alternative embodiment of the protrusive stent apparatus shown in FIG. 5a.

FIG. 11b is a longitudinal sectional view of a portion of a mammalian heart following completion of the procedure shown in FIG. 11a.

FIG. 13b is a cross sectional view through line 13b—13b of FIG. 13a.

FIG. 13c is an elevational view of the membrane covering and optional end cap (dotted lines) of the blocker device of FIG. 13a.

FIG. 13d is an elevational view of the radially expandable wire frame of the blocker device of FIG. 13a.

FIGS. 14a'–14b' are shematic, staged showings of the operation of a partial-occlusion pressure delay valve of the present invention which utilizes an annular balloon filled w/viscous fluid as the occluder member.

DETAILED DESCRIPTION OF THE PREFERRED EMBODIMENTS

The following detailed description and the accompanying drawings are provided for purposes of describing and illustrating presently preferred embodiments of the invention only, and are not intended to limit the scope of the invention in any way.

Upon making reference to the accompanying figures, it will be noted that many of the figures include showings of human cardiovascular anatomy. The various anatomical structures shown in the figures are labeled in accordance with the following legend:

AO . . . Aorta
CBV . . . Coronary Blood Vessel (artery, vein or man-made passageway)
CA . . . Coronary Artery
CAL . . . Coronary Artery Lumen
CV . . . Coronary Vein
CVL . . . Coronary Vein Lumen
IVC . . . Inferior Vena Cava
SVC . . . Superior Vena Cava
LV . . . Left Ventricle
RV . . . Right Ventricle
IVS . . . Intraventricular Septum
M . . . Myocardium I. TMDCR Method Wherein Transmyocardial Passageway is Formed Between a Chamber of the Heart and a Coronary Vein With reference to FIGS. 1–4, the present invention includes methods for improving perfusion of regions of the myocardium M which are ischemic or otherwise affected by the existence of an obstruction OB within a coronary artery CA, by forming a transmyocardial passageway 10 which extends from a chamber of the heart, (e.g., left ventricle LV), to a coronary vein CV.

Figure 1:
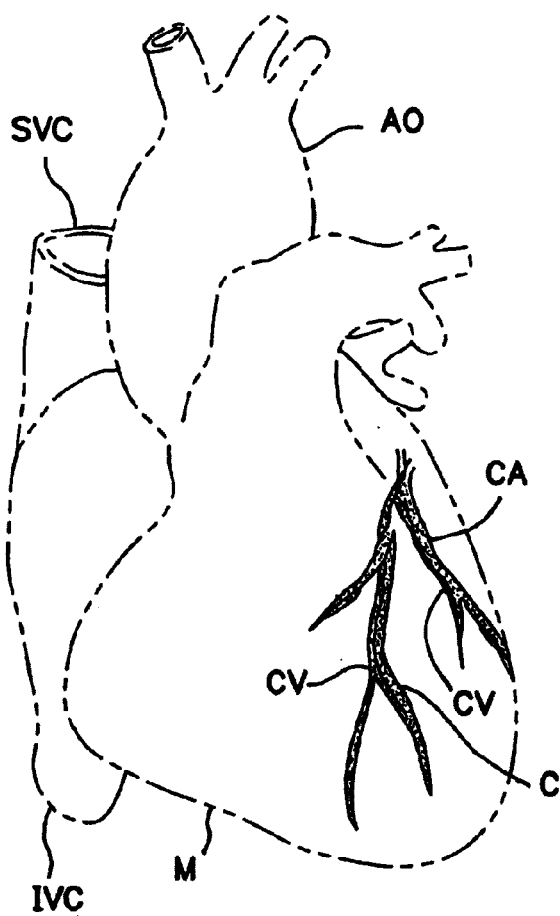
FIG. 1 is a perspective view of a human heart showing the typical anatomical positioning of the coronary arteries and coronary veins of the left heart.
Figure 1A:
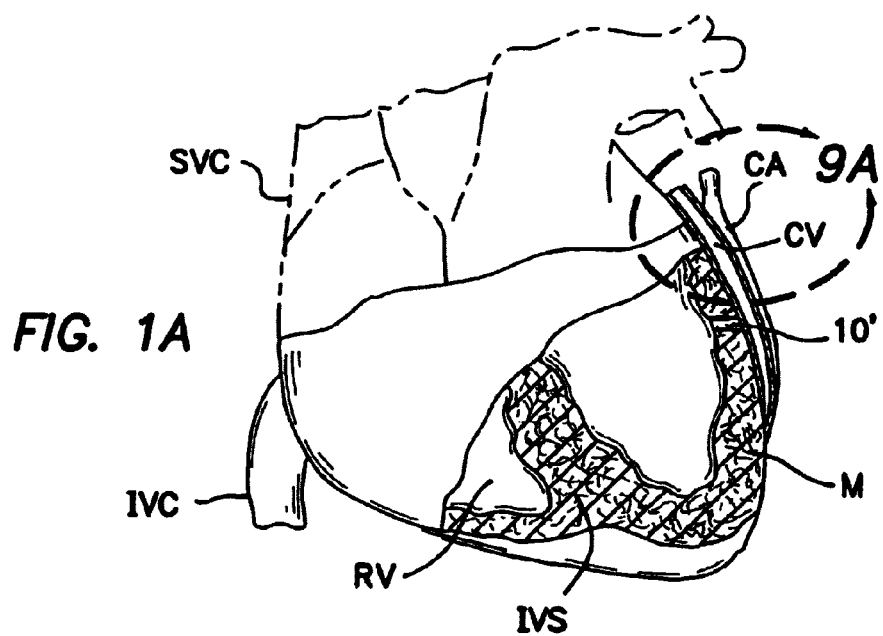
FIG. 1a is a partial cut-away sectional view of a human heart wherein a transmyocardial passageway has been created between the left ventricle and a coronary vein, in accordance with the present invention.
Figure 1B:
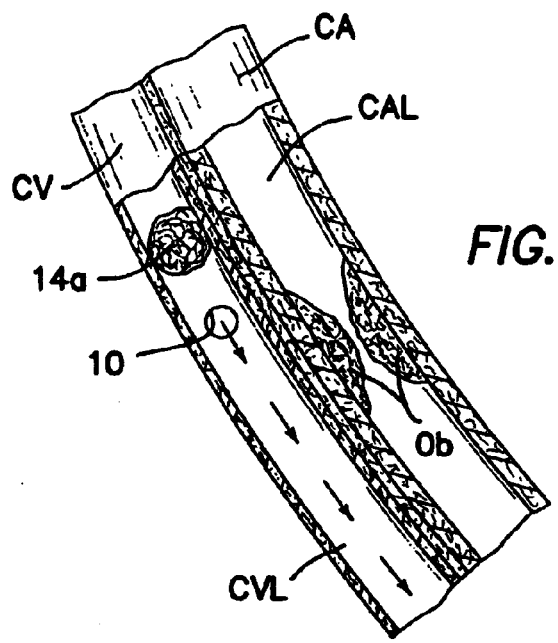
FIG. 1b is a partial longitudinal sectional view through an obstructed coronary artery and adjacent coronary vein, showing a transmyocardial passageway of the present invention, extending between the chamber of the left ventricle and the coronary vein.

In some embodiments of this method, the transmyocardial passageway 10 will simply provide a flow of blood from the chamber of the heart and into the coronary vein CV, such that the blood will pass in retrograde fashion through the coronary vein CV to perfuse the ischemic portion of the myocardium through the coronary vein, as sheen in FIG. 1b.

Figure 1D:
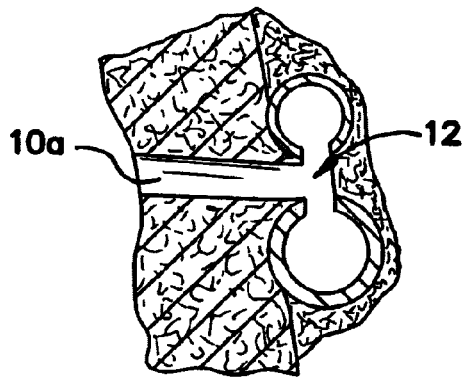
FIG. 1d is a partial longitudinal sectional view through a portion of the myocardium of a human heart, adjacent the left ventricle, showing an alternative embodiment of the present invention wherein a transmyocardial bloodflow passageway extends from the chamber of the left ventricle to a secondary passageway which has been created between the obstructed coronary artery and the adjacent coronary vein.
Figure 1C:
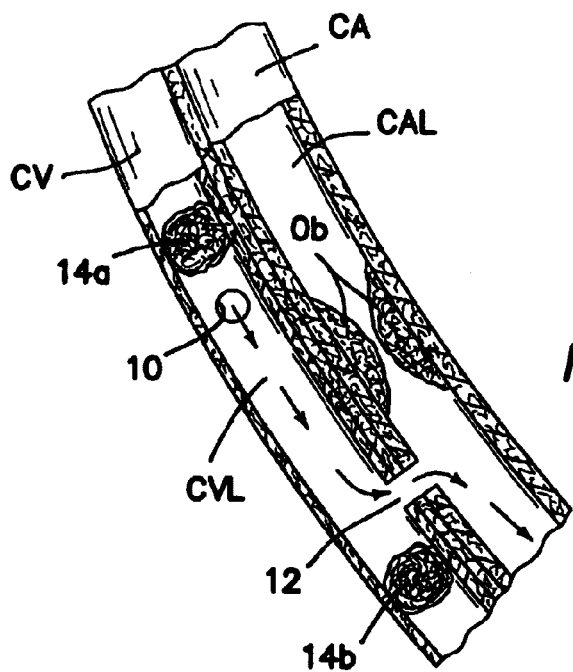
FIG. 1c is a partial longitudinal sectional view through an obstructed coronary artery and adjacent coronary vein, showing a transmyocardial passageway of the present invention extending between the chamber of the left ventricle to the coronary vein, and a secondary bloodflow passageway extending from the coronary vein to the adjacent coronary artery, downstream of the obstruction.
Figure 2:
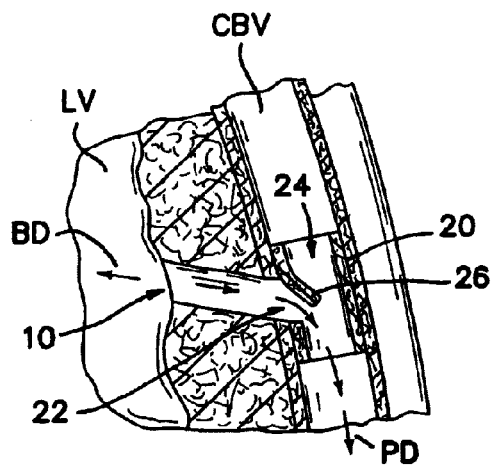
FIG. 2 is a longitudinal sectional view showing a first embodiment of an intravascular valving apparatus of the present invention operatively positioned within a coronary blood vessel (artery, vein or man-made passageway).

In other embodiments of the invention, a secondary bloodflow passageway 12 may be created between the coronary vein CV into which the transmyocardial passageway 10 extends and the obstructed coronary artery CA, at a location which is downstream of the obstruction OB, as shown in FIG. 1c. The formation of this secondary bloodflow passageway 12 allows blood from the chamber of the heart (e.g., the left ventricle LV) to initially flow through the transmyocardial passageway 10, through a segment of the coronary vein lumen CVL, through the secondary bloodflow passageway 12, and into the coronary artery lumen CAL, at a location downstream of the coronary artery obstruction OB, as shown in FIG. 2b. The secondary bloodflow passageway 12 which extends between the coronary vein Cv and the coronary artery CA may optionally be stented or internally supported by a stent, sleeve or coating (e.g., a polymer coating) to maintain patency of the secondary passageway 12.

In at least some applications, the coronary vein lumen CVL may be purposely blocked (e.g., ligated, embolized, fused, welded, clamped, etc.) at site(s) upstream and/or downstream of the transmyocardial passageway 10. As shown in FIG. 1b, when the transmyocardial passageway 10 formed for the purpose of shunting oxygenated blood into the coronary vein lumen CVL, a proximal embolization member 14a may be positioned within the coronary vein lumen CVL, immediately upstream of transmyocardial passageway 10, to ensure that the shunted blood will flow, in the desired retrograde direction through the coronary vein CV. Similarly, as shown in FIG. 1c, when a secondary bloodflow passageway 12 is formed to carry the oxygenated blood from the coronary vein lumen CVL into the coronary artery lumen CAL, downstream of the obstruction OB, a distal embolization member 14b may be positioned within the coronary vein lumen CVL immediately downstream of the secondary bloodflow passageway 12, to divert the flow of blood through the secondary bloodflow passageway 12.

Examples of methods for forming the optional secondary bloodflow passageway(s) 12 between the coronary vein CV and coronary artery CA are described in U.S. Provisional Specification Nos. 60/005,164, filed Oct. 13, 1995 and 60/010,614 filed Feb. 2, 1996, the entire disclosures of which are expressly incorporated herein by reference.

The proximal embolization member 14a and/or distal 14b embolization member may comprise any suitable type of lumen blocking matter or apparatus, examples of which are the embolization coils described in U.S. Pat. No. 5,382,260 (Dormandy, Jr. et al.), U.S. Pat. No. 5,108,407 (Geremia et al.), and U.S. Pat. No. 5,256,146 (Ensminger, et al.). Alternatively, the coronary vein lumen CVL may be closed off at the sites of the proximal 14a and/or distal 14b embolization members by any suitable alternative means, such as clamping, clipping, ligating, fusing, welding or adhesively conjoining the inner walls of the coronary vein lumen CVL so as to provide the desired blocking of bloodflow therethrough.

FIG. 1d shows an alternative embodiment of the method of the present invention wherein a secondary bloodflow passageway 12 of the above-described type has been created between the coronary vein CV and coronary artery CA, and wherein the transmyocardial bloodflow passageway 10a extends from the chamber of the heart (e.g., left ventricle) such secondary bloodflow passageway 12.

Figure 11A:
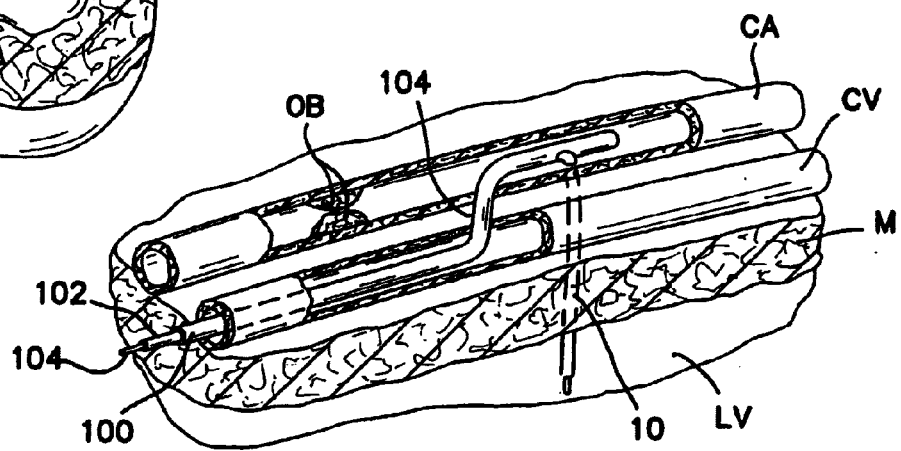
FIG. 11a is a partial section view through a portion of a mammalian heart showing the first stage of a transluminal coronary revascularization procedure wherein a temporary arterio-venous fistula is used to pass a passageway forming catheter into an obstructed coronary artery, downstream of the obstruction.
Figure 11B:
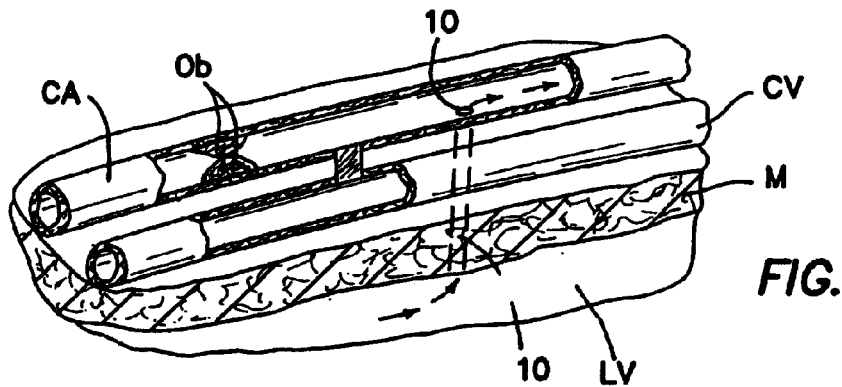

II. TMDCR Procedures Wherein Temporary A-V Fistula is Used to Facilitate Formation of Transmyocardial Passageway Entering Coronary Artery Downstream of Obstruction or Other Intraluminal Procedure FIGS. 11a–11b show an alternative TMDCR procedure of the present invention wherein a passageway-forming catheter 100 is initially advanced into a coronary vein CV which is situated adjacent a coronary artery CA in which an obstruction OB is present. When the distal end of the passageway-forming catheter 100 has been advanced to a location which is adjacent the segment of the coronary artery CA downstream of the obstruction OB, the passageway forming catheter 100 is oriented appropriately and a tissue-penetrating element 102 is passed out of the catheter 100, through the wall of the coronary vein, through any tissue located between the coronary vein CV and coronary artery CA, through the wall of the coronary artery CA and into the lumen of the coronary artery CA at a site downstream of the obstruction OB. In this manner, an arterio-venous passageway 104 is formed between the coronary vein CV and coronary artery CA.

After the distal end of the tissue-penetrating member 102 is advanced into the lumen of the coronary artery, a guidewire 104 is advanced through a lumen formed in the tissue-penetrating element 102 such that the guidewire enters the lumen of the coronary artery CA. Thereafter, the tissue-penetrating element 102 may be retracted into the catheter 100, and the catheter 100 may be further advanced over the guidewire 104 such that the distal portion of the catheter will pass through the arterio-venous passageway 104 and into the lumen of the coronary artery. Thereafter, the guidewire 104 is once again retracted into the tissue-penetrating element 102 and the catheter 100 is rotationally reoriented, as necessary, to direct the tissue-penetrating element 102 toward the left ventricle LF. Thereafter, the tissue-penetrating element 102 is advanced from the catheter 100, through the wall of the coronary artery CA, through the myocardium M and into the left ventricle LV. This results in the formation of a transmyocardial passageway 10 in accordance with the present invention. If desired, the guidewire 104 may then be once again passed through the lumen of the tissue-penetrating element 102 and into the left ventricle LV such that the tissue-penetrating element 102 may be retracted into the catheter 102 while the guidewire 104 remains extended through the transmyocardial passageway 10 and into the left ventricle LV. In this manner, the guidewire 104 may be used to guide the advancement of one or more passageway-modifying devices, and/or the placement of an internal sleeve, stent, valve or other apparatus within the transmyocardial passageway 10 as known in the prior art, described herein, or described in applicant's earlier filed U.S. patent application Ser. Nos. 08/730,327 and 08/730,496 and the corresponding counterparts thereof filed internationally under the PCT.

Thereafter, with the tissue-penetrating element 102 and guidewire 104 retracted into the catheter 100, the catheter 100 is extracted and removed from the body. The arteriovenous passageway 104 is then closed off (i.e., sealed, fused, cauterized, blocked, occluded, plugged, or otherwise closed) thereby preventing subsequent passage of blood between the coronary vein CV and coronary artery CA. In this manner, as shown in FIG. 11b, this procedure of the present invention results in the formation of a transmyocardial passageway 10 between the left ventricle Lv and a coronary artery CA, such that blood may pass from the left ventricle LV, through the transmyocardial passageway 10 and into the lumen of the coronary artery CA, downstream of the obstruction OB. The passage of the tissue-penetrating catheter 100 in the manner described hereabove and shown in FIG. 11a eliminates any necessity for advancing the catheter through the obstruction, and avoids the potential dislodgement of portions or particles of the obstruction OB into the coronary circulation.

It will be appreciated that any type of cauterizing, fusing, suturing or blocking apparatus may be used to close off the arterio-venous passageway 104, including at least some of the blocking devices described in applicant's above cited previously filed applications.

III. Other Procedures Which May Be Performed Using the Temporary A-V Passageway

It will be appreciated those skilled in the art that the temporary arterio-venous passageway 104 described hereabove in Section ii. May also be used for various other therapeutic or interventional procedures wherein it is desirable to gain access to the lumen of a blood vessel, downstream of an occlusion. This temporary arterio-venous passageway 104 is particularly suitable for use in procedures wherein a total or near total occlusion is present in the blood vessel so as to render it difficult or impossible to pass a catheter through the occlusion. The types of therapeutic or interventional procedures which may be performed through the temporary arterio-venous passageway 104 include, but are not necessarily limited to, balloon angioplasty, atherectomy, thrombolysis, placement of apparatus (e.g., a signal emitting target) within the lumen of the blood vessel downstream of the obstruction, or revascularization procedures such as the TMDCR procedure described hereabove.

This aspect of the invention may be particularly usable in patients who have previously undergone coronary artery bypass surgery, for bypassing of a total or near total occlusion. In such patients, it is common for new occlusions to occur at sites downstream of the anastomosis which connects the bypass graft to the occluded artery. IN such patients, it may be desirable to access the portion of the artery downstream of the occlusion to pass a balloon angioplasty catheter, atherectomy catheter, or other interventional device so as to treat such occlusions which may occur subsequent to performance of bypass surgery.

IV. TMDCR Procedures Using Unstented Transmyocardial Passageway

The present invention also includes alternative TMDCR methods wherein a transmyocardial passageway 10 is formed between a chamber of the heart and a coronary vessel (i.e., a) an endogenous coronary vein, b) an endogenous coronary artery, c) a man-made passageway in the heart which connects to an endogenous coronary vein; d) a man-made passageway in the heart which connects to an endogenous coronary or e) a man-made passageway which extends between an endogenous coronary artery and an endogenous coronary vein), and such transmyocardial passageway 10 is allowed to remain non-stented (e.g., devoid of any stent or internal support member positioned therewith).

The utilization of a non-stented transmyocardial passageway 10 in accordance with this embodiment of the present invention eliminates the need for precise measurement, pre-cutting to length and insertion of a stent apparatus within the transmyocardial passageway 10, as is required of the previous TMDCR method described in U.S. Pat. No. 5,287,861 (Wilk), U.S. Pat. No. 5,409,019 (Wilk) and U.S. Pat. No. 5,429,114 (Wilk). When the non-stented transmyocardial passageway 10 of the present invention is intended to provide bloodflow from the chamber of the heart (e.g., left ventricle) into the coronary vessel (e.g., vein, artery or man-made passageway), the non-stented transmyocardial passageway 10 must remain open during systolic contraction of the myocardium. If the non-stented passageway 10 is permitted to substantially occlude or close-off during systolic contraction of the myocardium, such could prevent or deter the desired blood flow from passing through the transmyocardial passageway 10. In this regard, in embodiments of the invention which utilize the non-stented transmyocardial passageway 10, it may be desirable to debulk, core or otherwise enlarge the diameter of the passageway 10 during it's formation so as ensure that the passageway 10 will remain patent and open, even during systolic contraction of the myocardium. Such coring, debulking or other enlargement of the passageway 10 may be accomplished by any suitable means, including the use of a hollow coring needle, laser, electrosurgical probe, or other tissue removing/ablating device capable of debulking and removing tissue so as to create a transmyocardial passageway 10 of the desired diameter.

Also, it will be appreciated that the non-stented transmyocardial passageway preferably should not fill-in with granulation tissue or otherwise close-off as a result of any scarring or healing process of the myocardium. In this regard, the coring, de-bulking or other enlargement of the non-stented passageway 10 and/or the continuing passage of blood, therethrough, may be sufficient to prevent or deter such scarring or natural closing of the non-stented passageway 10. However, in applications wherein scarring or natural closing of the non-stented passageway 10 is a potential problem, it may be desirable to cauterize, heat, chemically treat or coat the walls of the non-stented passageway to prevent or deter blocking of such passageway by scarring or ingrowth of the myocardial tissue.

Figure 3:
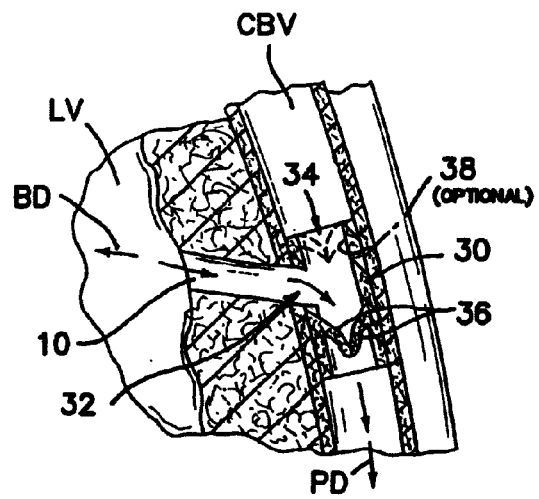
FIG. 3 is a longitudinal sectional view of a second embodiment of an intravascular valving apparatus of the present invention operatively positioned in a coronary blood vessel (artery, vein or man-made passageway).
Figure 4:
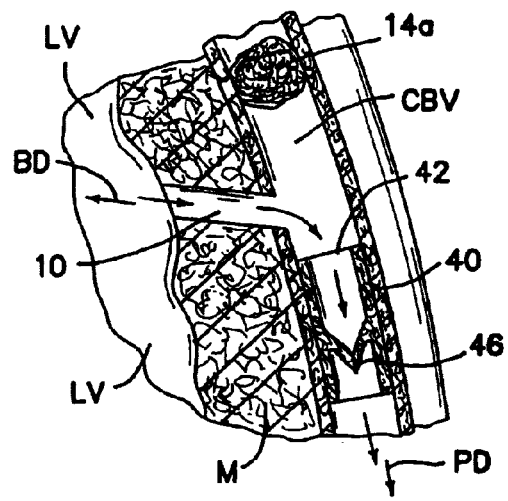
FIG. 4 is a longitudinal sectional view showing a third embodiment of an intravascular valving apparatus of the present invention operatively positioned within a coronary blood vessel (artery, vein or man-made passageway).

VII. Valving Apparatus Positionable in the Coronary Vessel(s) to Prevent Backflow Into the Transmyocardial Bloodflow Passageway In many embodiments of the invention, the transmyocardial passageway 10, 10a may function in it's intended manner without the inclusion of any valving apparatus, for intermittently blocking the flow of blood therethrough. However, in at least some applications, it may be desired to prevent the backflow of blood through the transmyocardial passageway 10, 10a during certain phase(s) of the cardiac cycle when the relative hemodynamic pressures would tend to cause such backflow. In this regard, the present invention includes intravascular valving apparatus 20, 30, 31, 33, 40, examples of which are shown in FIGS. 2–4. These intravascular valving apparatus 20, 20, 31, 33, 40 are positionable within the lumen of the coronary blood vessel CBV (e.g., vein, artery or man-made passageway), and operate to prevent backflow of blood into the transmyocardial bloodflow passageway 10, 10a.

In general, each of the intravascular valving apparatus 20, 30, 31, 33, 40 of the present invention comprise a radially expandable cylindrical or tubular body which is transluminally advanceable into the lumen of the coronary blood vessel CBV (e.g., artery, vein or man-made passageway), and which is then radially expandable so as to become implanted at a location which is adjacent or near to the intersection of that coronary vessel CBV with a transmyocardial bloodflow passageway 10, 10a. The valving apparatus 20, 30, 31, 33, 40 has an axial bore 24, 34, 42 through which blood may pass as it flows through the lumen of the coronary blood vessel CBV or secondary passageway 12 in which the apparatus 20, 30, 31, 33, 40 is positioned. One or more occluder members 26, 36, 46 are formed within the apparatus 20, 30, 31, 33, 40. Such occluder member(s) 26, 36, 46 are alternately moveable between a first (e.g., open) position whereby blood is permitted to flow from the transmyocardial bloodflow passageway into the coronary blood vessel CBV or secondary passageway 12, and a second (e.g., closed) position whereby blood is prevented or deterred from backflowing or regurgitating from the coronary blood vessel CBV or secondary passageway 12, into the transmyocardial bloodflow passageway.

Individual embodiments of the intravascular valving apparatus 20, 30, 31, 33, 40 are described in more detail herebelow. It will be appreciated, however, that each of the intravascular valving apparatus 20, 30, 31, 33, 40 of the present invention offer advantages over the intramyocardial stenting/valving apparatus described in U.S. Pat. No. 5,248,861 (Wilk), U.S. Pat. No. 5,409,019 (Wilk) and U.S. Pat. No. 5,429,144 (Wilk) in that they are operatively situated entirely within the lumen of the coronary blood vessel CBV of secondary passageway 12 and do not extend into the transmyocardial passage way (e.g., the first passageway 10, 10a) which emanates from the chamber (e.g., left ventricle) of the heart. In this regard, the valving apparatus 20, 30, 31, 33, 40 of the present invention do not require precise measurement or precise cutting-to-length, as is purportedly required of the intramyocardial stenting/valving apparatus described in U.S. Pat. No. 5,248,861 (Wilk), U.S. Pat. No. 5,409,019 (Wilk) and U.S. Pat. No. 5,429,144 (Wilk).

It is desirable that the valving apparatus 20, 30, 31, 33, 40 of the present invention be initially disposable in a first radially compact diameter which is small enough to be mounted upon or inserted into an intravascular delivery catheter. Such intravascular delivery catheter, having the valving apparatus 20, 30, 31, 33, 40 mounted thereon or therewithin, is transluminally passable through the vasculature and into the lumen of the coronary blood vessel CBV wherein the apparatus 20, 30, 31, 33, 40 is to be implanted. Thereafter, the apparatus 20, 30, 31, 33, 40 is radially expanded (by self-expansion or pressure-expansion) to a second radially expanded diameter, wherein the outer surface of the apparatus 20, 30, 31, 33, 40 frictionally engages the surrounding wall of the coronary blood vessel CBV such that the apparatus 20, 30, 31, 33, 40 is thereby implanted and retained in a stationary position. When the valving apparatus 20, 30, 31, 33, 40 is so implanted within the coronary blood vessel CBV, blood may flow through the axial bore 24, 34, 42 of the apparatus 20, 30, 31, 33, 40, as described in more detail herebelow. It is to be appreciated that the valving apparatus 20, 30, 31, 33, 40 may be either self-expanding or pressure-expandable. In this regard, if the valving apparatus 20, 30, 31, 33, 40 is "self-expanding", the cylindrical body of the apparatus 20, 30, 31, 33, 40 may be formed of a shape memory alloy or resilient material (e.g., spring metal) which is inherently biased to it's second radially expanded diameter. Alternately, in embodiments wherein the valving apparatus 20, 30, 31, 33, 40 is "pressure-expandable", the cylindrical body of the apparatus 20, 30, 31, 33, 40 may be formed of plastically deformable material which is initially formed it's first radially compact diameter, and which may be pressure deformed to it's second radially expanded diameter by the exertion of outward force from an internally positioned balloon or other radial expansion device.

It is to be further appreciated that the potential useability and applicability of the intravascular valving apparatus 20, 30, 31, 33, 40, 50 described herebelow is not limited only to uses in connection with the improved TMDCR methods of the present invention, but may also be useable as a modification of the previously described TMDCR methods, such as those of U.S. Pat. No. 5,287,816 (Wilk), U.S. Pat. No. 5,409,019(Wilk), and U.S. Pat. No. 5,429,144 (Wilk).

a. Intravascular Valving Apparatus - First Embodiment

Figure 2A:
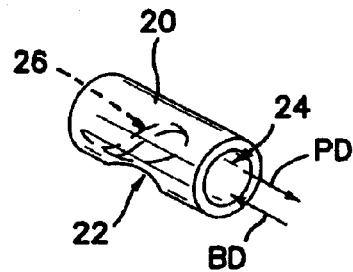
FIG. 2a is a perspective view of the intravascular valving apparatus of FIG. 2.
Figure 2B:
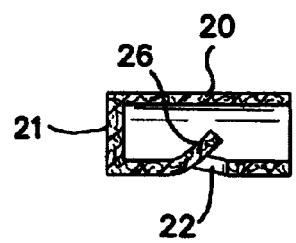
FIG. 2b is an elevational view of a variant of the intravascular valving apparatus shown in FIGS. 2 and 2a, wherein a bloodflow blocking bulkhead is formed on the upstream end of the apparatus.

FIGS. 2, 2a and 2b show a first embodiment of an intravascular valving apparatus 20 which is positioned within the lumen of a coronary blood vessel CBV (artery, vein or man-made passageway), at a location which is adjacent it's intersection with the transmyocardial passageway 10. This embodiment of the valving apparatus 20 has a cylindrical body having an axial bore 24 which extends longitudinally therethrough, and a side aperture 22 formed in the sidewall thereof. The side aperture 22 is preferably the same size or larger than the diameter of the adjacent end of the transmyocardial passageway 10, such that blood flowing from the cardiac chamber (e.g., left ventricle LV) through the transmyocardial passageway 10 will pass directly through the side aperture 22 and into the bore 24 of the valving apparatus 20. An occluder member 26, such as a hinged obturator or pliable elastomeric leaflet is affixed to the cylindrical body of the valving apparatus 20, and extends over and substantially blocks the side aperture 22 so as to prevent the flow of blood out of the side aperture 22. The occluder member 26 is alternately moveable between a first position wherein it blocks blood from flowing out of the side aperture 22, and a second position wherein it permits blood to flow into the bore 24 through the side aperture 22.

This first embodiment of the valving apparatus 20 may be implanted in the lumen of the coronary blood vessel CBV such that the side aperture 22 is in alignment with the adjacent end of the bloodflow passageway 10. During systolic contraction of the heart the relatively high pressure within the left ventricle will force the occluder member 26 to its second (open) position, allowing blood to flow from the left ventricle, through the transmyocardial passageway 10, through the side aperture 22, through the bore 24 and into the lumen of the coronary blood vessel CBV in the perfusive direction PD, as shown. Thereafter, during systolic relaxation of the heart, the relatively low filling pressure within the left ventricle LV will draw the occluder member 26 to its first (closed) position whereby the occluder member 26 will prevent blood from regurgitating or moving in the backflow direction BD from the lumen of the coronary blood vessel CBV, out of the side aperture 22, and into the bloodflow passageway 10. In this manner the first embodiment of the valving apparatus 20 serves to facilitate efficient pumping of oxygenated blood from the left ventricle and into the lumen of the coronary blood vessel CBV, to improve the flow of oxygenated blood to an ischemic or blood-flow-deprived region of the myocardium M.

As shown in FIG. 2a, a closure member 21, in the nature of an end cap, may be formed on the upstream end of the apparatus 20 so as to completely or substantially block the flow of blood through the coronary blood vessel CBV and into the upstream end of the bore 24 of the apparatus 20. The optional inclusion of the end closure member 21 in the apparatus 20 may serve to obviate any need for the placement of a proximal embolization member 14a within the lumen of the coronary blood vessel CBV, upstream of the valving apparatus 20.

b. Intravascular Valving Apparatus - Second Embodiment

FIG. 3 shows a second embodiment of the intravascular valving apparatus 30 which comprises a generally cylindrical body having an axial bore 34 extending longitudinally therethrough and a pair of occluder members 46 positioned therewithin, and a side aperture 32 formed in the cylindrical sidewall of the apparatus 30, behind the occluder members 36. Each occluder member 36 is affixed at least one point to the cylindrical body of the apparatus 30, and may comprise any suitable structure or openable and closeable passage, such as a self-sealing slit or hole, or a hinged leaflet or pliable elastomeric member. The occluder members 46 are alternately moveable between first positions wherein the occluder members 36 directly contact one another so as to prevent blood from backflowing in the backflow direction BD through the axial bore 34 of the apparatus 30, and second positions wherein the occluder members 36 move out of contact with one another such that blood may flow through the axial bore 34 of the apparatus 30 in the perfusion direction PD. The side aperture 32 is preferably as large as or larger than the diameter of the bloodflow passageway 10 which extends through the myocardium M from the left ventricle LV to the lumen of the coronary blood vessel CBV. This embodiment of the apparatus 30 is implanted in the lumen of the coronary blood vessel CBV such that its side aperture 32 is directly aligned with the bloodflow passageway 10 so that blood may flow through the bloodflow passageway 10, into the axial bore 34 of the apparatus 30.

During systolic contraction of the heart the relatively high pressures created in the left ventricle LV will force blood to flow through the passageway 10 into the axial bore 34 of the valving apparatus 30. Such systolic bloodflow will move the occluder members 36 to their second (i.e., open) positions, thereby allowing the blood to flow through the lumen of the coronary blood vessel in the perfusion direction PD. Thereafter, when the heart undergoes diastolic relaxation, the relatively low filling pressures created within the left ventricle LV will draw the occluder members 36 to their first (ie. closed) positions, thereby preventing blood from regurgitating or backflowing out of the side aperture 32, in the backflow direction BD. In this manner, this second embodiment of the intravascular valving apparatus 30 serves to facilitate efficient pumping of oxygenated blood from the left ventricle LV and through the lumen of the coronary blood vessel CBV, in order to provide improved bloodflow to an ischemic or blood-flow-deprived region of the myocardium M.

Optionally, secondary occluder members 38 may be formed or mounted within the bore 34 of the apparatus 30, upstream of the side opening 32. These optional secondary occluder members 38 may be of the same type and construction as the above-described downstream occluder members 36. If present, such additional occluder members 38 will assume their first (e.g., closed) position when the pressure of blood within the bore 34 of the apparatus 30 downstream of such secondary occluder members 38 is greater than the pressure of blood within the coronary blood vessel CBV upstream of the such secondary occluder member 38. In this regard, the provision of such secondary occluder members 38 within the apparatus 30 will obviate the need for placement of a proximal occlusion apparatus 14a within the lumen of the coronary blood vessel CBV upstream of the transmyocardial bloodflow passageway 10. The inclusion of such secondary occluder members 38, or the alternative use of a proximal occlusion member 14a, will be of particular importance when the coronary blood vessel CBV is a coronary vein CV, due to the substantial difference between endogenous coronary venous blood pressures and those pressures which will be created by systolic arterial bloodflow through the coronary vein, downstream of the transmyocardial bloodflow passageway 10.

Figure 3A:
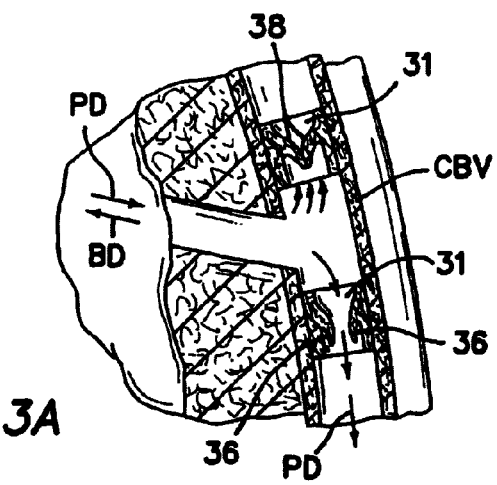
FIG. 3a is longitudinal sectional view showing variant of the second intravascular valving apparatus embodiment shown in FIG. 3, wherein two (2) separate valving apparatus are respectively positioned upstream and downstream of the junction between the transmyocardial bloodflow passageway and the coronary blood vessel (artery, vein or man-made passageway).

FIG. 3a shows one variant of the second embodiment wherein two (2) separate intravascular valving apparatus 31a, 31b are respectively positioned upstream and downstream of the transmyocardial bloodflow passageway. The above-described occluder members 36 are formed in the apparatus 31b which is positioned downstream of the transmyocardial bloodflow passageway 10 and the above-described secondary occluder members 38 are formed within the apparatus 31a which is positioned upstream of the transmyocardial bloodflow passageway 10. In this manner, these separate intravascular valving apparatus 31a, 31b, will function in the same manner as the apparatus 30 shown in FIG. 3, when it is equipped with the optional secondary occluder members 38. However, it will be appreciated that these separate intravascular valving apparatus 31a, 31b do not have any side aperture 32, as does the device shown in FIG. 3, and accordingly, will obviate any need for correctly sizing an aligning such side aperture 32 with the transmyocardial bloodflow passageway 10.

Figure 3B:
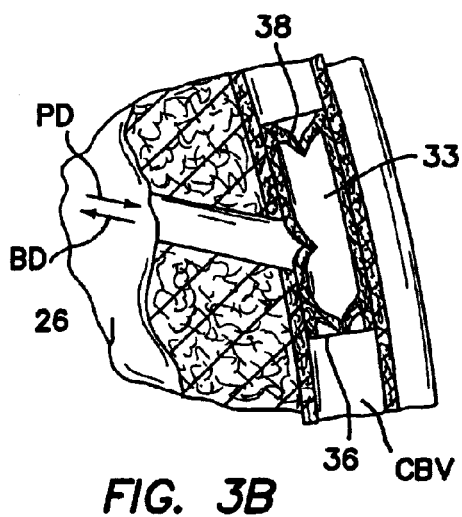
FIG. 3b is a longitudinal sectional view of another variant of the second intravascular valving apparatus embodiment shown in FIG. 3, wherein three (3) valves are incorporated within a single tubular body to accomplish valving of bloodflow through a transmyocardial bloodflow passageway and coronary blood vessel (artery, vein or man-made passageway).

FIG. 3b shows another variant of the second embodiment wherein a single intravascular valving apparatus 33, in the nature of a tubular stent or tubular body, is provided with three (3) separate valves 26, 36, 38 at locations which are a) at the junction of the transmyocardial passageway 10 and the coronary blood vessel CBV, b) upstream of the transmyocardial passageway 10 and c) downstream of the transmyocardial passageway 10, respectively. These valves 26, 36, 38 may comprise self-sealing pliable slit openings, elastomeric leaflets, hinged occluder members or any other suitable type of structure or apparatus which will intermittently open and close, to permit bloodflow in the desired direction therethrough. For example, in applications wherein it is desired for the transmyocardial passageway 10 to provide a flow of blood from the cardiac chamber into the coronary blood vessel CBV, the first valve 26 will operate to open during systole to permit blood to flow from the transmyocardial passageway 10 into the coronary blood vessel CBV, but will close during diastole to prevent backflow or regurgitation into the cardiac chamber. Similarly, the second (upstream) valve 38 will close during systole to prevent backflow of blood through the proximal end opening of the valving apparatus 33. The third (downstream) valve 36 will open during systole to permit the desired flow of blood entering through the transmyocardial passageway 10, to continue on downstream through the coronary blood vessel CBV in the desired perfusion direction.

c. Intravascular Valving Apparatus - Third Embodiment

FIG. 4 shows a third embodiment of the intravascular valving apparatus 40 which comprises a generally cylindrical body having an axial bore 42 extending longitudinally therethrough and a plurality of occluder members 46 formed therewithin. The cylindrical body and occluder members 46 of this third embodiment of the apparatus 40 are the same as those of the above described second embodiment, except that the cylindrical body of this third embodiment is devoid of any side aperture(s) or openings in the cylindrical sidewall. In contrast to the above described second embodiment 30, this third embodiment of the apparatus 40 is implanted in the lumen of the coronary blood vessel CBV at a location which is downstream of the junction between the coronary blood vessel CBV and the first bloodflow passageway 10.

It will be appreciated that the individual features and attributes of each of the above-described embodiments of valving apparatus 20, 30, 31, 33, 40 may be incorporated into any or all of the other above-described valving apparatus 20, 30, 31, 33, 40 as feasible, to accomplish the desired hemodynamic bloodflow within the coronary vasculature.

Figure 5:
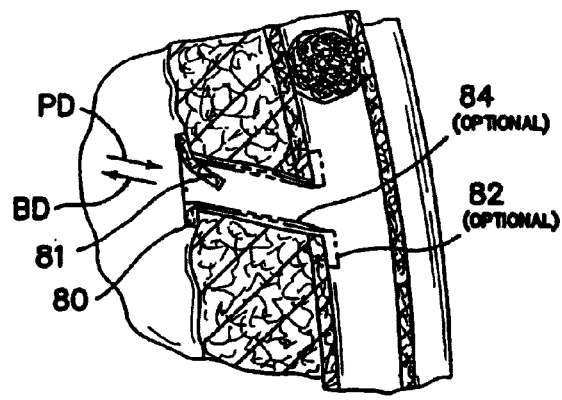
FIG. 5 is a longitudinal sectional view showing an intracardiac valving apparatus of the present invention along with an optional retainer assembly (dotted lines) useable to mount such intracardiac valving apparatus on the inner wall of the heart.
Figure 5A:
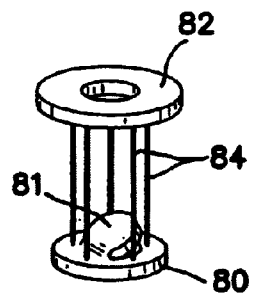
FIG. 5a is a perspective view of the intracardiac valving apparatus of FIG. 4 having the optional retainer assembly affixed thereto.

VI. Intracardiac Valving Apparatus For Controlling Bloodflow Through the Transmyocardial Passageway FIGS. 5 and 5a show examples of intracardiac valving apparatus 80 which may be utilized to prevent backflow of blood through the transmyocardial passageway 10, or to otherwise control the flow of blood through the transmyocardial passageway 10 in accordance with the systolic/diastolic cardiac cycle.

As shown, the intracardiac valving apparatus 80 is positionable within the cardiac chamber (e.g., left ventricle) immediately adjacent the opening of the transmyocardial passageway 10 thereinto. The intracardiac valving apparatus 80 may comprise any suitable type of hinged, pliable or moveable occlusion member or self-sealing slit which will operate to intermittently block or unblock the flow of blood in at least one direction through the transmyocardial passageway 10. In the embodiment shown in FIGS. 5, 5a, the intracardiac valving apparatus 80 comprises a generally annular body having a central aperture formed therein and an occluder member 81, such as a pliable elastomeric flap, mounted within the aperture. The occluder member 81 will move, in relation to hemodynamic bloodflow and/or contraction of the myocardium M, between an open position whereby blood is permitted to pass in at least one direction through the transmyocardial passageway 10, and a closed position whereby blood is prevented from flowing in at least one direction through the transmyocardial passageway 10.

The intracardiac valving apparatus 80 may be implanted within the cardiac chamber by any suitable surgical or non-surgical technique. Preferably, the intracardiac valving apparatus 80 is initially positioned within or upon a delivery catheter, and the delivery catheter is advanced through the coronary blood vessel CBV, and through the transmyocardial passageway 10. Thereafter, the intracardiac valving apparatus 80 is released or ejected from the delivery catheter, and is caused to radially expand to it's operative configuration. the expanded valving apparatus 80 is then retracted into abutting contact with the myocardial wall, as shown.

The intracardiac valving apparatus 80 may be attached to the myocardial wall by any suitable attachment such as hooks, sutures, adhesives or a retaining assembly which is operative to hold the intracardiac valving apparatus 80 in its desired fixed position upon the myocardial wall. One such retaining apparatus, shown in FIGS. 5 and 5a, comprises an annular retaining ring 82 which is positionable within the coronary blood vessel CBV and a plurality of elastomeric tether members 84 which extend between the retainer ring 82 and the intracardiac valving apparatus 80. In this manner, the elastomeric tethers 84 will resiliently draw the retaining ring 82 and intracardiac valving apparatus 80 toward one another, so as to hold the intracardiac valving apparatus 80 in fixed abutment with the myocardium M as shown.

In some embodiments of the intracardiac valving apparatus 80, the occluder member 81 will be designed to move in response to changes in hemodynamic pressure, such that when the hemodynamic pressure within the cardiac chamber (e.g., left ventricle) exceeds that within the transmyocardial passageway 10, the occluder member 81 will move to it's open position, and when the pressure within the transmyocardial passageway 10 exceeds that within the cardiac chamber (e.g., left ventricle) the occluder member 81 will move to it's closed position.

Alternatively, in other embodiments of the intracardiac valving apparatus 80, the occluder member 81 may be designed to move in relation to contractile changes in the myocardial muscle. In these embodiments, the occluder member 81 will be mechanically linked or coupled to the body of the intracardiac valving apparatus 80 such that, when the myocardium undergoes contraction (e.g., shortening and thickening), the occluder member 81 will be propelled to it's open position, and when the myocardium undergoes relaxation (e.g., lengthening and narrowing) the occluder member 81 will move to it's closed position.

In this manner, the intracardiac valving apparatus 80 of the present invention serves to control the desired bloodflow through the transmyocardial passageway 10, without the need for customizing or precise cutting-to-size of any intramyocardial stent, as has been described in the prior art.

VII. Tissue Valve for Preventing Backflow into the Transmyocardial Bloodflow Passageway An alternative to the use of the above-described intravascular valving apparatus 20, 30, 31, 33, 40 and/or the intracardiac valving apparatus 80, is an endogenous tissue valve which may be formed within the transmyocardial passageway 10 or at either end thereof. For example, FIGS. 6a–6b show an endogenous tissue valve 50 which is formed at the junction of the transmyocardial bloodflow passageway 10 and a coronary blood vessel CBV (e.g., artery vein or man-made passageway).

Figure 6A:
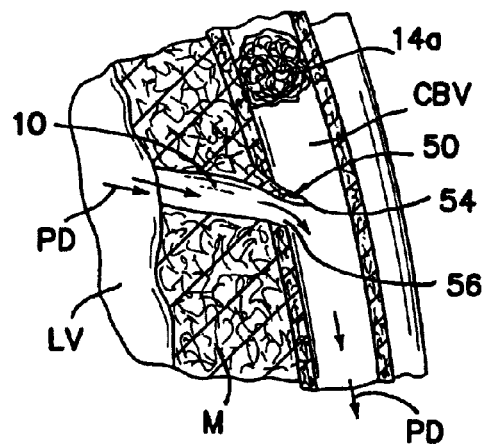
FIGS. 6a and 6b are longitudinal sectional views of a human heart wherein a bloodflow passageway has been created between the left ventricle and a coronary blood vessel (artery, vein or man-made passageway), and a valving tissue valve has been created in the wall of the blood vessel, in accordance with the present invention.
Figure 6B:
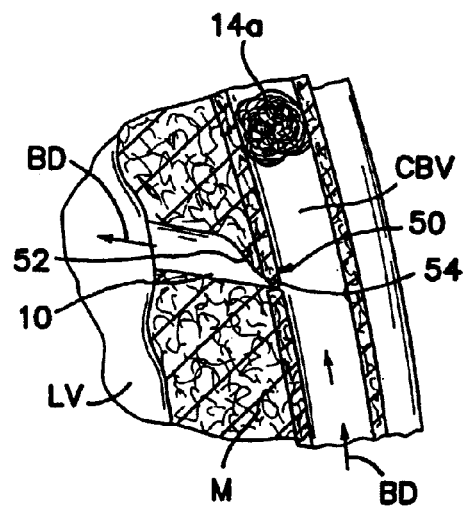

With reference to FIGS. 6a–6b, the endogenous tissue valve 50 may comprise one or more segment(s) 54 of the wall of the coronary blood vessel CBV, along with one or more tapered segment(s) of underlying myocardial tissue 52.

This endogenous tissue valve 50 is formed such that the segment(s) of blood vessel wall 54 and underlying portion(s) of myocardial tissue 52 will receive sufficient blood supply so as not to become necrotic or infarcted. The thickness and mass of the tissue valve 50 is preferably defined so that, when the heart undergoes systolic contraction the elevated pressure created within the left ventricle LV and transmyocardial bloodflow passageway 10 will force the tissue valve 50 to an open position, as illustrated in FIG. 5a, thereby creating an opening 56 through which blood may flow into the lumen of the coronary blood vessel CBV, in the profusion direction PD. Thereafter, when the heart undergoes diastolic relaxation the relatively low filling pressures within the left ventricle LV and transmyocardial bloodflow passageway 10 will allow the tissue valve 50 to return to a second or closed position, as illustrated in FIG. 5b. When in such second or closed position, the tissue valve 50 will substantially or completely close off the transmyocardial bloodflow passageway 10, so as to prevent blood from backflowing or regurgitating in the backflow direction BD, from the lumen of the coronary blood vessel CBV into the transmyocardial bloodflow passageway 10.

The tissue valve 50 may be created by any suitable means, including a procedure whereby the tissue penetrating, cutting or boring device used to create the transmyocardial bloodflow passageway is provided with a tapered distal end having a configuration analogous to that of the inner edge(s) 55 of the wall segment(s) 54 so as to form the desired tissue valve(s) or segment(s) when form the endogenous tissue valve 50, or by another catheter-based device which is equipped to form such tissue valve(s) or segment(s).

It will be appreciated that the tissue valve 50 may be formed in various configuration. For example, although the tissue valve 50 shown in FIGS. 6a and 6b hereof consists of a single flap, various alternative configurations may be utilized wherein multiple tissue protrusions, multiple tissue flaps, or angularly tapered or funnel shaped tissue flaps are formed to perform the desired valving function. Any and all such configurations of endogenous tissue are intended to be included within the scope of the term "tissue valve" 50 as used herein.

VIII. Elastic Closure for Preventing Backflow Into the Transmyocardial Bloodflow Passageway An alternative to the mechanical valving apparatus 20, 30, 31, 33, 40 or endogenous tissue valve 50 is the elastic closure member 60, shown in FIGS. 7a and 7b.

The elastic closure member 6d may comprise one or more sutures formed of stretchable or elastic material such as latex or other elastomeric polymer materials. Such elastic closure member(s) 60 are preferably passed through adjacent portions of myocardial tissue next to the opening 66 between the transmyocardial bloodflow passageway 10 and the lumen of the coronary blood vessel CBV (or secondary bloodflow passageway 12).

Figure 7A:
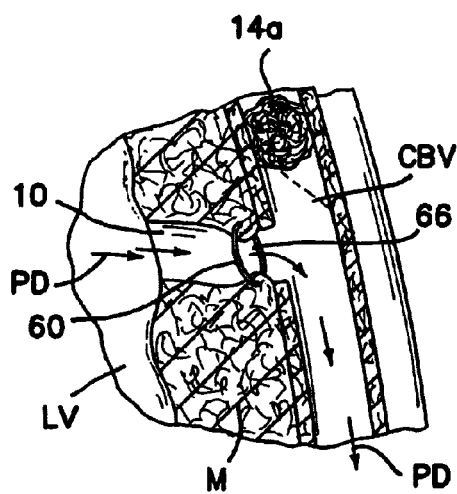
FIGS. 7a–7b are longitudinal sectional views of a human heart wherein a blood vessel passageway has been created between the left ventricle and a coronary blood vessel (artery, vein or man-made passageway), and wherein an elastic suture has been positioned, in accordance with the present invention.
Figure 7B:
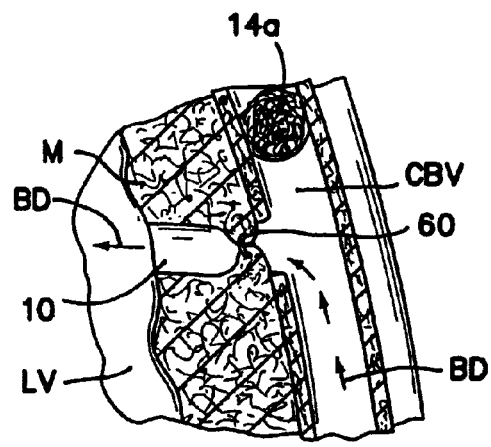

The elastic closure member(s) 60 is the elastically biased to a retracted state whereby the closure member(s) 60 will draw the adjacent portions of myocardium M together so as to close off the opening 66 between the transmyocardial bloodflow passageway 10 and the lumen of the coronary bloodflow CBV, as shown in FIG. 7b. Upon systolic contraction of the heart the relatively high pressures created within the left ventricle LV and transmyocardial bloodflow passageway 10 will cause the elastic closure member(s) 60 to stretch or expand, thereby forming opening 66 through which blood may flow from the transmyocardial bloodflow passageway 10 into the lumen of the coronary blood vessel CBV (or secondary bloodflow passageway 12) in the perfusion direction PD, as shown in FIG. 7a.

Thereafter, when the heart undergoes diastolic relaxation the relatively low filling pressures within the left ventricle LV and transmyocardial bloodflow passageway 10 will allow the elastic closure member 60 to retract, thereby closing off the opening 66 and preventing blood from backflowing or regurgitating from the lumen of the coronary blood vessel CBV (or secondary bloodflow passageway 12) into the transmyocardial bloodflow passageway 10, in the backflow direction BD, as shown in FIG. 7b.

It will be appreciated that the elastic closure member 60 may be installed in any suitable method, such as by way of an appropriate suturing or stapling device which operates to attach the elastic closure member 60 at its desired location. Such installation of the elastic closure member 60 may be accomplished by open surgical technique or by way of catheter-based, transluminal methodology. For example, a catheter having a suturing or stapling device positioned therewithin may be advanced to a position adjacent the opening 66. Thereafter, negative pressure or other suitable drawings means may be utilized to draw adjacent segments of the myocardial tissue, from either side of the transmyocardial passageway 10, into the catheter. Thereafter, the desired elastic closure member 60 may be penetrated and threaded through the adjacent sides of the myocardial tissue so as to form the desired elastic closure member 60, as shown.

IX. Protrusive Stents and Stented Grafts for Stenting of the Transmyocardial Passageway In accordance with another aspect of the invention shown in FIGS. 8a–8c, protrusive stents or stented grafts may be positioned within the transmyocardial passageway 10, and may extend into one or more adjacent coronary vessels including a) an endogenous coronary vein, b) an endogenous coronary artery, c) a man-made passageway in the heart which connects to an endogenous coronary vein, d) a man-made passageway in the heart which connects to an endogenous coronary artery and/or e) a man-made passageway which extends between an endogenous coronary vein and an endogenous coronary artery. sA described more fully herebelow, the protrusive stent apparatus 90, 90a, 90b of the present invention may incorporate one or more valving apparatus to intermittently block or direct bloodflow in accordance with various stages of the systolic/diastolic cardiac cycle. Furthermore, such protrusive stent apparatus may optionally be covered or juxtapositioned to a tubular graft or sheath so as to form a discrete tubular passageway.

Figure 8A:
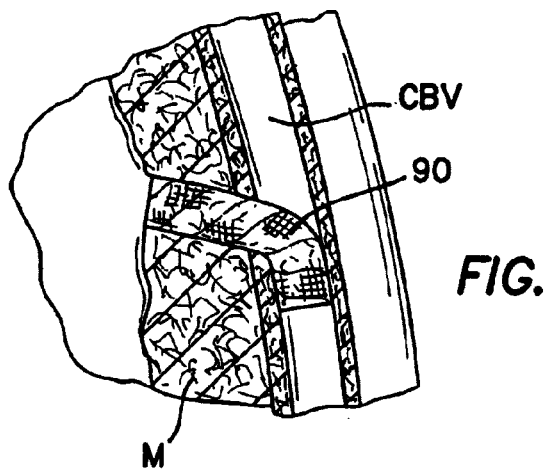
FIG. 8a is a longitudinal sectional view showing a protrusive stent apparatus of the present invention implanted within a transmyocardial passageway and extending into a coronary blood vessel (e.g., artery, vein or man-made passageway).

FIG. 8a shows a non-valved, non-covered protrusive stent apparatus 90 of the present invention positioned partially within a transmyocardial passageway 10, and extending into the coronary vessel CV (e.g., artery, vein or man-made passageway) to which such transmyocardial passageway 10 extends. As shown, the protrusive stent apparatus 90 is curved or bent at the junction of the transmyocardial passageway 10 and the coronary vessel Cv, and preferably extends into the coronary vessel CV in the desired bloodflow direction.

The protrusive stent apparatus 90 may be formed of any suitable material, such as wire mesh or other metal or polymeric material, and may be self-expanding or pressure-expandable.

Figure 8B:
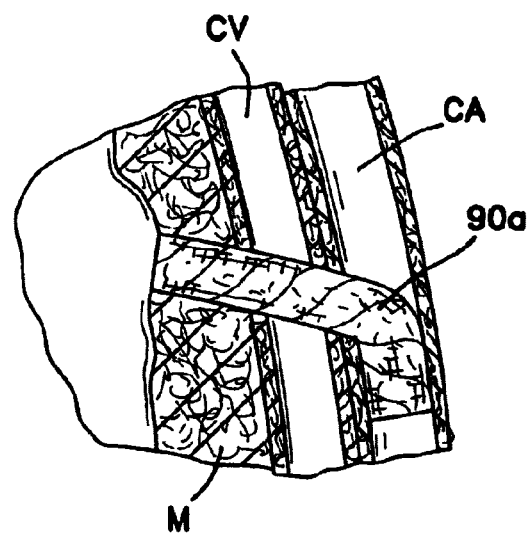

FIG. 8b shows a variant of the protrusive stent apparatus 90a positioned partially within a transmyocardial passageway 10, extending through a coronary vein CV, through a secondary passageway 12, and into a coronary artery CA. As shown the protrusive stent apparatus 90a is curved or bent at the junction of the secondary passageway 12 and the coronary artery CA and preferably extends into the coronary artery CA in the desired bloodflow direction.

Figure 8C:
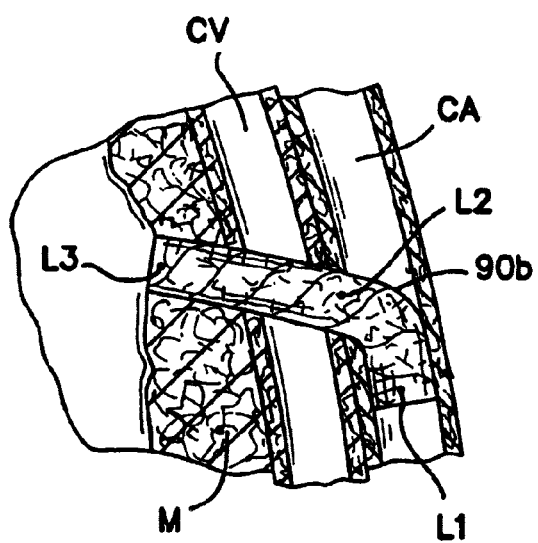
FIG. 8c is a longitudinal sectional view showing another alternative embodiment of the protrusive stent apparatus shown in FIG. 5a, having an optional tubular covering and/or optional valve(s) incorporated therein.

FIG. 8c shows alternative variations of the protrusive stent apparatus 90b wherein an optional tubular covering 92 is formed on the protrusive stent 90b. Such optional covering 92 may be any suitable tubular covering such as woven polyester or expanded, sintered polytetrafluoroethylene (PTFE). Additionally, or alternatively, one or more valves such as hinged occluder members or pliable elastomeric leaflets may be located within the protrusive stent apparatus 90b with or without covering 92, at locations $L_1$ and/or $L_2$ and/or $L_3$ to facilitate control and valving of bloodflow through the transmyocardial passageway 10, coronary vein CV, secondary passageway 12 and/or coronary artery CA. It will be appreciated that embodiments of the protrusive valving apparatus 90b which incorporates such valves at locations $L_1$ and/or $L_2$ and/or $L_3$ may be provided with appropriate openings or apertures in any covering 92 formed thereon to facilitate the desired inflow or outflow of blood at specific locations thereon.

These protrusive stent apparatus 90, 90a, 90b with or without the optional covering 92 and/or without the optional valves at locations $L_1$ and/or $L_2$ and/or $L_3$ offer advantages over previously known intramyocardial stents in that they do not require precise cutting to length or precise positioning within the myocardial passageway 10. Indeed, the protrusive stent apparatus 90, 90a, 90b of the present invention are intended to protrude into a coronary blood vessel CBV (e.g., artery, vein and/or man-made passageway) and the length of the portion of the stent apparatus 90, 90a, 90b which extends into such coronary blood vessel CBV is typically not critical. In this regard, there will exist no need for custom-fitting or precise pre-cutting of the stent apparatus 90, 90a, 90b prior to implantation within the patient.

In embodiments where the stent apparatus 90, 90a, 90b is covered by a partial or complete tubular covering, such covering may be formed of any suitable material including but not necessarily limited to polyester, woven polyester, polytetrafluroethylene, expanded polytetraflouroethylene, polyurethane; silicone, polycarbonate, autologous tissue and, xenograft tissue.

Figure 9:
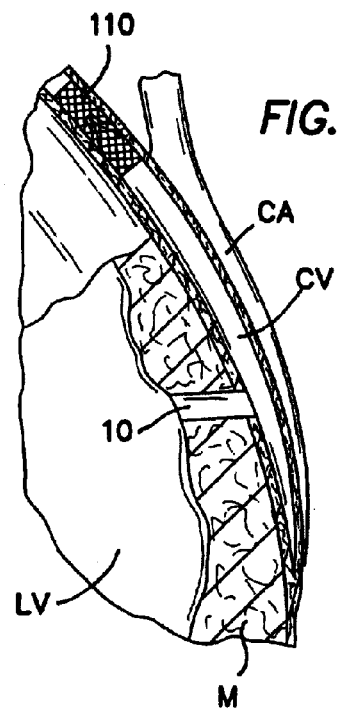
FIG. 9 is a partial sectional view of a portion of a mammalian heart wherein an intravascular valving apparatus has been positioned within a coronary vein to provide pressure-controlled intermittent coronary venous occlusion for enhanced coronary retroperfusion.
Figure 9A:
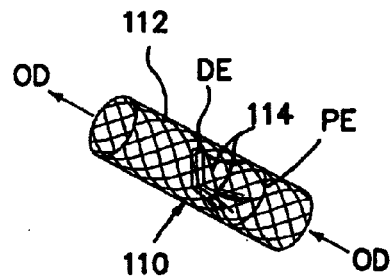
FIG. 9a is a perspective view of the intravascular valving apparatus shown in FIG. 9.
Figure 9B:
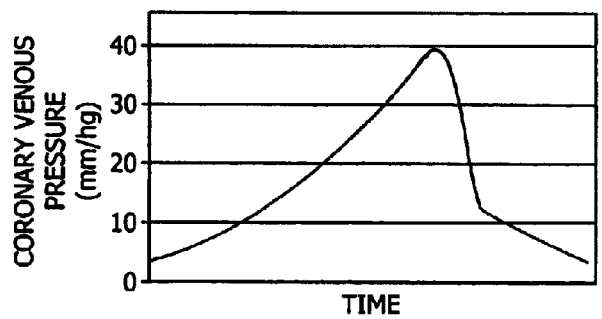
FIG. 9b is a graph of coronary venous pressure vs. time in a coronary vein having an intravascular valving apparatus of the present invention implanted therein.
Figure 9C:
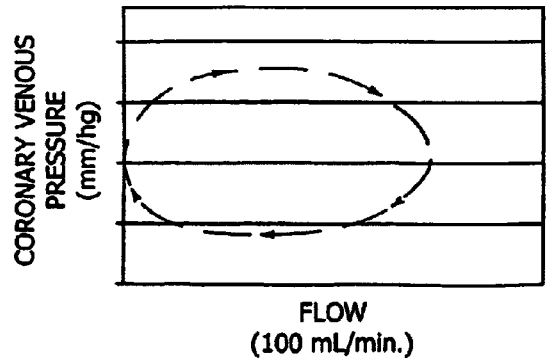
FIG. 9c is a draft of coronary venous pressure vs. flow in a coronary vein having an intravascular valving apparatus of the present invention implanted therein.

X. Intravascular Valving Apparatus and Method for Intermittent Coronary Venous Occlusion for Enhanced Coronary Perfusion or Regulation of Coronary Venous Pressure FIGS. 9—9b are illustrative of a method of the present invention wherein a valving device 110 is positioned within the coronary sinus, great cardiac vein or other coronary vein to control coronary venous pressure in a manner which results in increased dwell time of arterial blood within a myocardial capillary bed and/or dilation of the capillary bed and/or other improvement of perfusion of an ischemic region of the myocardium M.

The theory underlying the mechanism of total or partial venous occlusion, and various embodiments of valves useable to accomplish such full or partial venous occlusion, are further explained and shown in FIGS. 12a–19b.

Figure 12A:
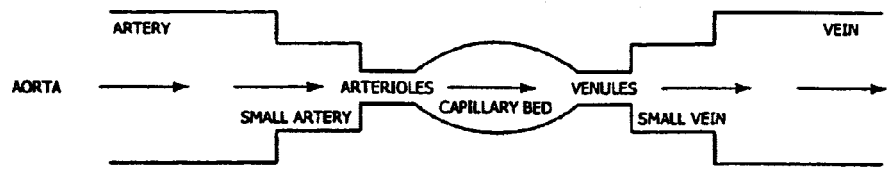
FIG. 12a is a shematic diagram of the flow of blood through the coronary vasculature without full or partial blocking of venous return in accordance with the present invention.
Figure 12B:
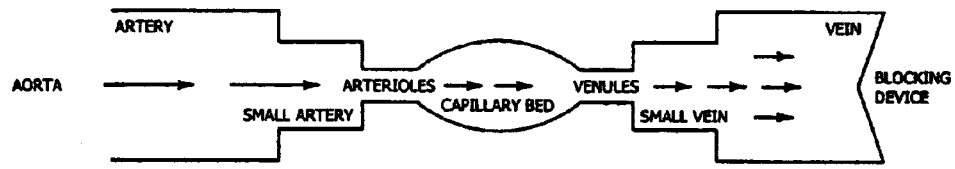
FIG. 12b is a shematic diagram of the flow of blood through the coronary vasculature with full or partial blocking of venous return in accordance with the present invention.
Figure 13A:
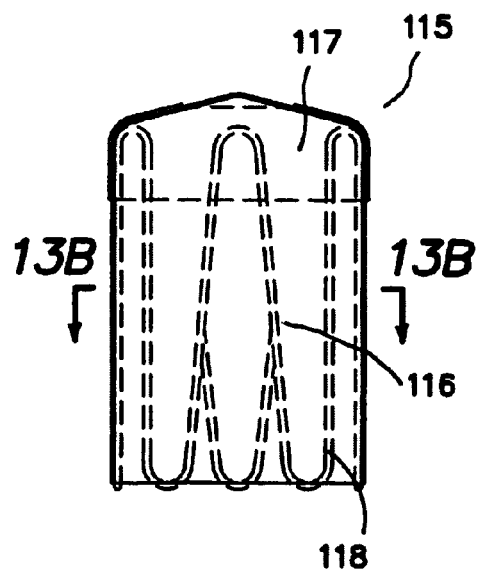
FIG. 13a is an elevational view of one embodiment of a coronay vein blocking device of the present invention having an optional end cap (dotted lines) disposed on the closed end thereof.
Figure 13B:
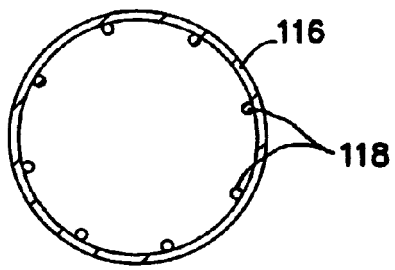
Figure 13C:
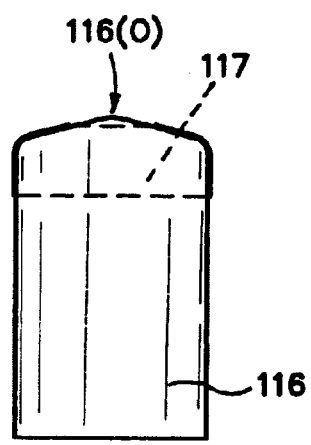
Figure 13D:
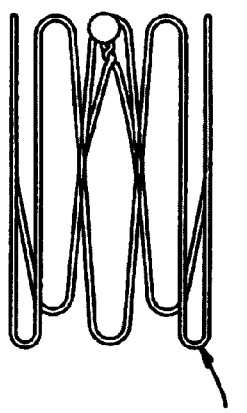
Figure 13E:
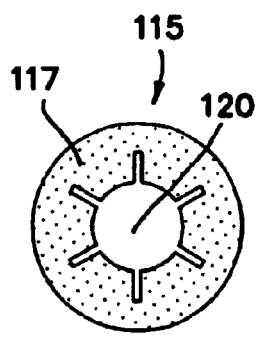
FIG. 13e is an end view of the device of FIG. 13C.

FIGS. 12a–12b provide a shematic diagram of the path of blood flow during normal, unrestricted flow (12a), and valved or blocked flow (12b). In the case of restricted or blocked venous flow, the outflow from the capillary bed is restricted thereby increasing the dwell time of the blood in the capillary bed, and allowing for the ischemic area to be in contact with oxygenated blood for an increased interval, providing the proposed therapeutic effect.

Several devices can be employed to achieve partial, total or intermittent venous occlusion. The range of therapeutic benefits will depend on the 1) placement of the devices in relation to the ischemic tissue, 2) the rate at which the heart's second venous system, the Thebesian system, compensates for the blockage and takes over the function of the venous flow through its capillary network, 3) the device used to create the occlusion, namely, the rate of blockage, and whether or not the blockage is valved, and 4) the extent of the collateralization that may already exist in the circulation. In the event the Thebesian system diverts venous flow and compensates for any flow taken off-line by the placement of a venous block, it may be necessary to valve the blocking device to provide a two-phase effect. In the first phase, Phase I, the valve is in a closed position, restricting the outflow from the capillary bed and providing the desired benefit. In the second phase, Phase II, the valve opens, releasing the flow into the venous system at an interval such that the Thebesian system does not begin compensating for the venous blockage and diminishing the therapeutic effect. In this embodiment the degree to which the flow is restricted is a function of both the magnitude of the restriction and its duration. A description of several embodiments follows that address the variations necessary to achieve desired therapeutic benefits in a given clinical application.

1. Total Occlusion of the Vein.

In patients with diffuse cardiovascular disease, therapeutic value may be achieved by totally blocking the venous system, e.g. continuously blocking blood flow through the vein.

a) Non-valved—As shown in FIGS. 13a–13e, total or partial occlusion can be achieved by implantation of a particular embodiment of the valaving device 110, such embodiment comprising a non-valved, cylindrical blocker 115. In its preferred construction, this blocker 115 comprises a cylindrical frame structure 118 which is fully or partially encased or covered by a tubular polymer 116 or fabric 117 covering or combination thereof. In a preferred embodiment, a sinusoidal wire frame structure 115 is covered with a silicone film 116. In addition to providing an occlusive surface 116(O), this covering 116 aids in shielding the thin walled vein from any trauma caused by the metal struts of the wire frame structure. It is appreciated that the frame structure of the blocker device 115 may be formed of various materials, including stainless steel, NiTi, platinum, titanium and the like. The structure of said frame can be wound wire, a slotted tube, expanded to a larger configuration, or coiled structure. Preferably, the frame structure will be formed of a material such as NiTi that will exert a constant force on the vessel wall, compensating for any enlargement of the vein due to the changes in pressure. In addition, it is appreciated that the blocker device may be fashioned in the form of a wedge-like geometry (not shown) to further ensure secure placement within the vessel.

In some cases, a cap of material is secured to the distal end of the blocking device, to aid in embolization, securement of the device upon placement in a vessel, and ultimately endothelialization (tissue ingrowth). Said cap, 117, can be formed of various materials including polyester fabric (e.g. Dacron™), PTFE, a high-porosity silicone or polyurethane. (see, PCT International Patent Application No. PCT/US97/01463 for further details, the contents of such application being expressly incorporated herein by reference.

b) Single Pressure Valve—As shown, the valving apparatus 110 of this invention may be positioned within a coronary vein, CV (or within the coronary sinus). The valving apparatus 110 may comprise a cylindrical framework or stent 112 having one or more occluder flaps 114 mounted axially therewithin. The occluder flaps 114 have proximal ends PE and distal ends, DE. The proximal ends PE of the occluder flaps 114 define an inflow opening, and the flaps 114 are alternately moveable between a closed configuration wherein the flaps 114 are in abutment with one another so as to block or prevent blood from flowing in the outflow direction OD, and an open configuration wherein the flaps 114 are sufficiently separated from one another to permit blood to flow through the valving apparatus in the outflow direction OD.

Figure 14A:
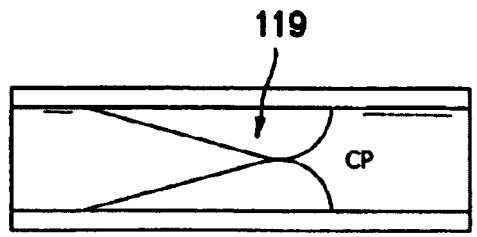
FIGS. 14a–14c are shematic, staged showings of the operation of a full-occlusion pressure delay valve of the present invention which utilizes an annular balloon filled w/viscous fluid as the occluder member.
Figure 14B:
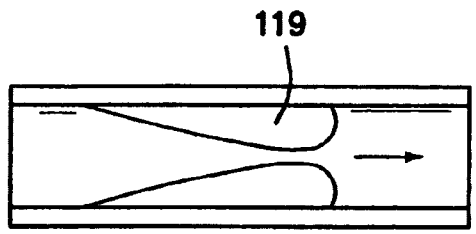
Figure 14C:
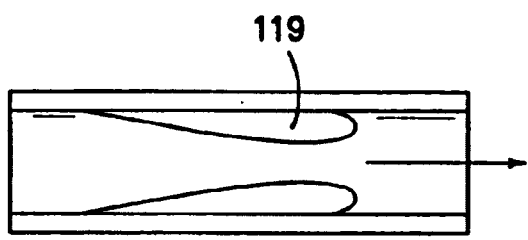
Figure 14A:
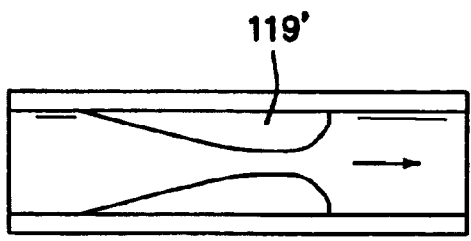
Figure 14B:
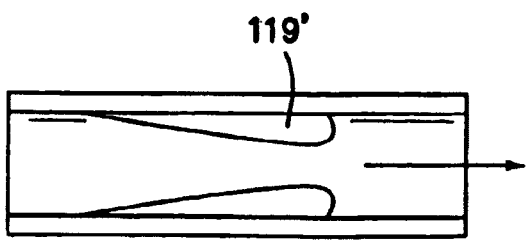
Figure 15:
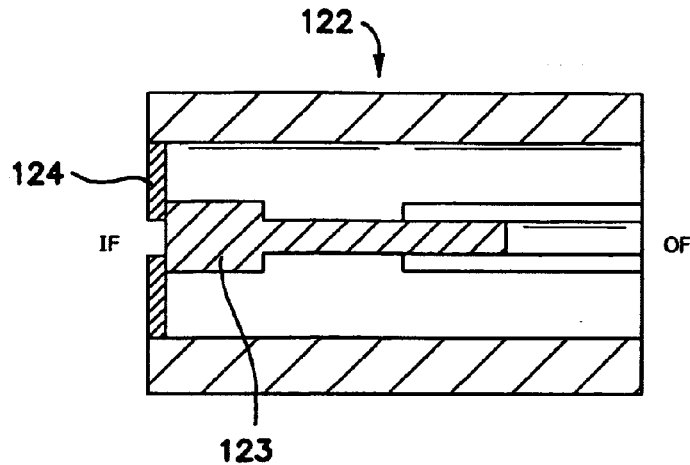
FIG. 15 is a shematic diagram of an implantable magnetic delay valve of the present invention in its closed position.
Figure 16:
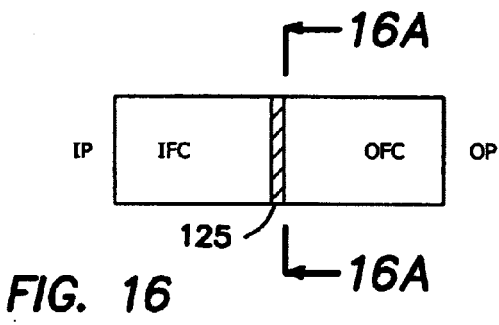
FIG. 16 is a shematic diagram of an implantable oxygen sensor delay valve of the present invention.
Figure 16A:
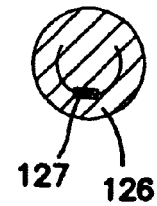
FIG. 16a is a cross sectional view through line 16a–16a of FIG. 16.
Figure 17:
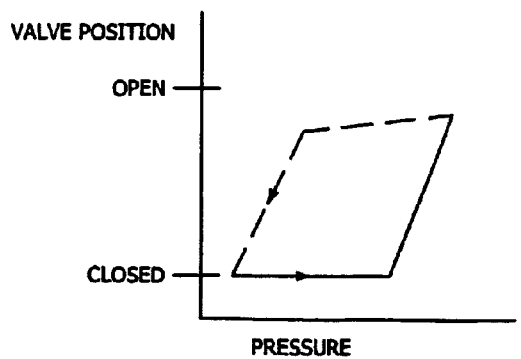
FIG. 17 is a graph of valve position vs. capillary pressure for any of the time delayed venous occlusion valves of the present invention.
Figure 18A:
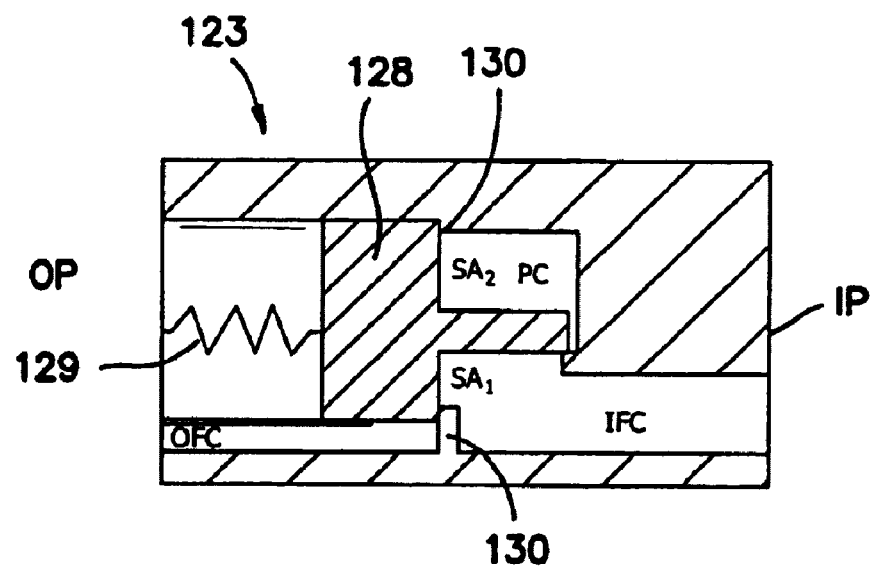
FIG. 18a is a schematic showing of a full-occlusion pressure delay valve of the present invention in its closed position.
Figure 18B:
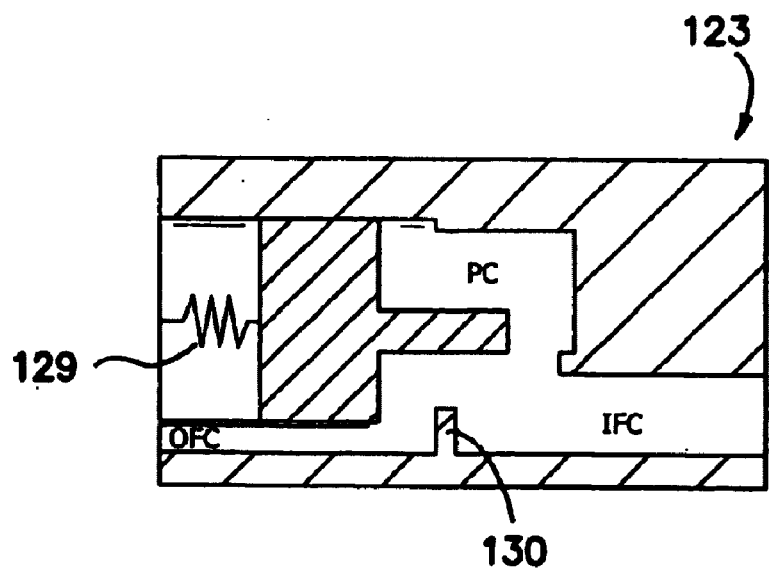
FIG. 18b is a schematic showing of a full-occlusion pressure delay valve of the present invention in its open position.
Figure 19A:
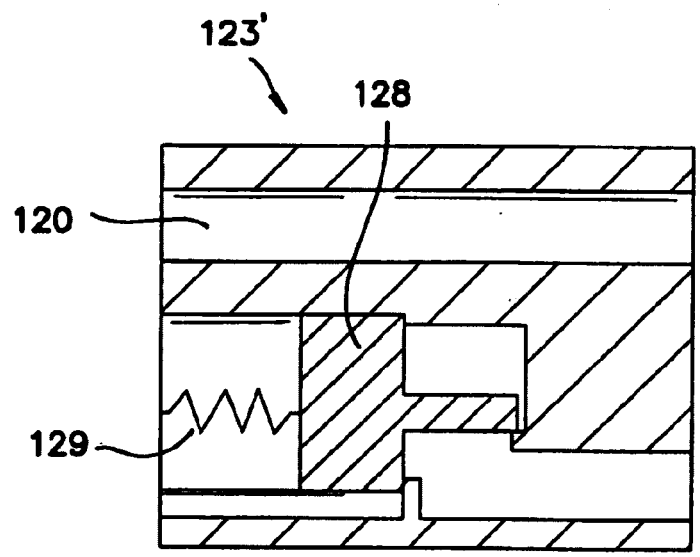
FIG. 19a is a schematic showing of a partial-occlusion pressure delay valve of the present invention in its closed position.
Figure 19B:
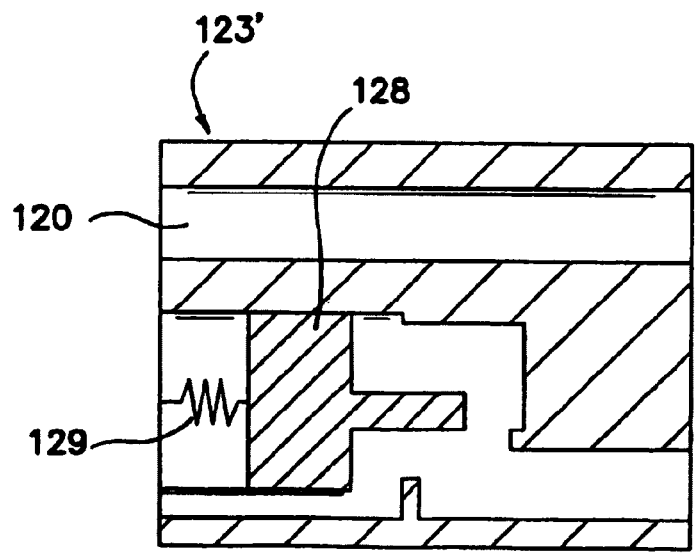
FIG. 19b is a schematic showing of a partial-occlusion pressure delay valve of the present invention in its open position.

In an alternative embodiment, valved structures can be employed that open and allow flow at a certain pressure (P), and close when the pressure goes below P. Certain valves known in the art such as a duckbill valve, slit valve, poppet valve, umbrella valve or like structures can be employed in this manner within an implantable structure for placement into the vein. c) Delayed Action Valve—In contrast to the single pressure valve, embodiments that provide for delayed valving may also be employed, enabling the blockage to be maintained for an extended period of time based on a fixed time delay or a lower closure pressure than that pressure required to open the valve. The length of delay or trigger for release of flow may be timed to the cardiac cycle to maximize the oxygenation phase, or Phase I, and minimize the effect of alternative venous return (such as the Thebesian veins). Examples of such delayed action valves 119, 122, 125, 123 are shown in FIGS. 14a–18b.

i) Time Delay Mechanism. In FIGS. 14a–14c and 14a'–14b', there are shown alternative embodiment of valves 119, 119' providing for a pressure activated, time-delayed full (119) or partial (119') venous occlusion. A tubular structure is provided with an outer lumen and an inner lumen, said inner lumen forming a flowable valve flap, 119, 119' containing a viscous substance, such as silicone gel filled balloon (shown), biased to a closed position CP as shown in FIG. 12a. As depicted in FIGS. 14b–c, one embodiment of the valve 119 is initially fullu closed and, upon being contacted by increasing inflow pressure, move to an open configuration and remain open for a period of time sufficient for the viscous substance to settle back to its original biased position. The time delay is a function of the viscosity of the flowable substance, which can be varied depending on the desired length of delay. A similar embodiment of the valve 119' shown in FIGS. 14a' and 14b' operates in the sa,e manner as the above-described valve 119, but does not completely occlude venous return even when in its fully closed state (FIG. 14a').

ii) Magnetic Valve. In a further embodiment as shown in FIG. 15 the valving apparatus comprises a tubular structure or valve body 122, having an inflow direction (IF) and an outflow direction (OF), and further having a valving member comprised of a substantially cylindrical ferrous element 123, detachably coupled with a fixed magnetic surface 124, located at the inflow IF end of the valve body. In a first or closed position, the valving member 123 and the magnetic surface 124 are coupled thereby blocking flow through the valve body. The magnetic force of the coupling between the valving member 123 and the magnetic surface 124 dictates the opening pressure of the valve. When the pressure exerted by blood flow in the inflow direction is sufficient to overcome the magnetic force of the coupling between the valving member 123 and the magnetic surface 124(P1 or opening pressure), the valving member 123 is dislodged, allowing flow to travel through the valve body. The time delay function of this embodiment occurs during the interval when the pressure in the inflow direction falls below P1 and the valving member 123 is drawn back into contact with the magnetic surface 124 of the valve body by the magnetic force existing between them.

iii) Oxygen sensor valve. With reference to FIGS. 16 and 16a, the time delay mechanism may also be a function of the level of oxygenation sensed by the valving apparatus. This embodiment of the valving apparatus is triggered to an open or closed position based upon the percent oxygenation it senses at its inlet port. In a further embodiment as shown in FIGS. 16 and 16a, this valving apparatus has an inlet port IP and and outlet port OP and a flowthrough lumen provided therebetween. A septum 125 disposed within the flowthrough lumen, thereby separating the valving apparatus into two chambers, and inflow chamber IFC and an outflow chamber OFC. Said septum 125 being comprised of a valved structure 126 having an oxygen sensor 127 mounted thereon. Said oxygen sensor 127 triggers the valve to be in an open or closed position, depending on the percent oxygenation in the inflowing blood. As blood flow travels into the inflow chamber IFC, it contacts the oxygen sensor 127. Said sensor maintains the valved structure in a closed position until a preset desired oxygen content is reached within the blood in the inflow chamber IFC. Upon sensing the desired, pre-set oxygenation level, the valved structure opens and releases flow into the outflow chamber OFC and the venous system.

d) Pressure Delay Mechanism. It may be desirable to have valve structures that open and close along a certain hysteresis curve as shown graphically in FIG. 17. In a first embodiment shown in FIG. 16, a device having a tubular structure with an inflow direction (IF) and outflow direction (OF), having a piston mechanism 128 that is set to open at a pressure (P1), and remain open until the pressure falls below P2, where P2 is less than P1. The piston 128 is biased towards a closed position with a spring-like member 129, which is secured to strut member on the outflow end of the device. In the closed position, the piston member abuts a ledge 130, provided by the inner contour of the tubular structure. Further defined by the inner contour of the tubular structure is an inlet port (IP) and an outlet port (OP) defining a flow path therethrough. In the closed position, a fluid seal is created between the piston and the ledge, thereby blocking flow between the inlet port IP and the outlet port OP, and defining certain chambers within the tubular structure; an inflow chamber (IFC), and outflow chamber (OFC), a pressure chamber (PC). In operation, the force on the piston in the closed position is equal to the pressure of the fluid at the inlet port IP multiplied by the surface area 1 (SA1). When the force exceeds a certain threshold $F_t$, the correlating pressure P1 will cause the piston to travel toward the OP, thereby compressing the spring mechanism 129, and allowing flow to travel from IFC to OFC. In the open position, fluid communication is established between the inflow chamber IFC and the pressure chamber PC, thus increasing the force on the piston by an amount equal to the pressure at the inlet port IP multiplied by surface area 2(SA2). The increased surface area allows a lower pressure P2 to generate sufficient force above that of the value of Ft, thereby maintaining the valve in the open position. When pressure decreases below P2, the valve will close and the hysteresis cycle can be repeated (i.e. the valve will not re-open until a pressure P1 is achieved.) In clinical application, this results in an intermittent occlusion of venous flow which may prevent the activation of alternative venous conduits such as the Thebesian veins. The desired crack open pressure and hold open pressure is a function of the spring force of spring member 129, and the values of SA1 and SA2 and can be varied depending on the activity intervals desired.

2. Partial Occlusion of the Vein. In a similar method to placing a total blocking system, a partial blocker may also be placed in an alternative embodiment, wherein flow through the valve body is never fully blocked, but is restricted to the degree necessary to achieve a therapeutic benefit.

a) Non-valved—In an embodiment similar to that described in FIG. 11, an opening, 120 can be formed in the distal tip of the blocking device, sufficient to provide for a certain amount of flow therethrough, while still providing a restriction sufficient to achieve a therapeutic effect.

b) Single Pressure Valve—Similarly, as shown in FIGS. 14a–c and 14a'–b', for example, in the case of the flowable valve, it is appreciated that the flaps of said valve may be positioned such that in the closed or fully biased position, they do not contact each other, thereby affecting a narrowing of flow through the valve body. In operation, the action of the valve in response to the inflow pressure of the blood flow (e.g. viscous biasing) varies the diameter of the narrowing, but does not act to totally occlude the valve lumen.

c) Delayed Action Valve—It may be desirable to provide the combined effect of a partial blockage (i.e. reduced by continuous flow) and a hysteresis, or delayed action valve. Toward this end, it is appreciated that the delayed action valve embodiments described above may additionally provide a flow through lumen-positioned within the tubular valving apparatus. For example, in the partial-occlusion embodiment of FIGS. 19a–19b, the pressure delay valving apparatus 123' includes a flow through lumen 120 which allows continuous flow through the valve body even when the occluder 128 is in its closed position (FIG. 19a), while in the full-occlusion embodiment shown in FIGS. 18a–18b, no flow-through passageway is provided and, when the occluder 128 is in its closed position (FIG. 18a) the flow of blood through the vein will be totally blocked.

3. Method of Implantation

Femoral or jugular vascular access is gained to the venous system via standard sheath and dilator placement in the femoral or jugular vein. A coronary sinus access catheter is placed to cannulate the coronary sinus to assist in the placement of guidewires into the GCV and AIV over which subsequent interventional devices will be placed, including the blocking devices described hereabove. A coronary sinus guide catheter (not shown), with introducer dilator is advanced over the GCV/AIV wire until the tip of the guide is deep seated past the "mouth" of or entrance to the coronary sinus. The introducer dilator is then removed. A blocker delivery catheter, Not shown is advanced over the GCV/AIV guidewire under flouroscopy to a position in the vein approximate the ischemic segment. The GCV/AIV guidewire is then removed, and a blocker is inserted into the proximal end of the delivery catheter. A push rod, (not shown) is then inserted into the blocker delivery catheter, and the blocker device is pushed until it exits the delivery catheter and expands into position in the vein.

The positioning of the blocker varies depending on the location of the ischemic region. Preferably, a blocker is placed in the vein to occlude the specific venous return flow from the region. It is appreciated that it may be necessary to block multiple small veins, or the larger main venous conduits fed by the smaller veins.

A transmyocardial passageway 10 of the present invention may optionally, but not necessarily, be formed between a chamber of the heart such as the left ventricle LV and the coronary vein CV such that oxygenated blood may enter the lumen of the coronary vein CV to enhance the retroperfusion of the myocardium M.

The flaps 114 of the valving apparatus 110 are constructed so as to be biased to their closed configuration, but so as to separate and move to their open configuration when the pressure of blood exerted against the flaps 114 in the outflow direction OD exceeds a predetermined maximum amount. This causes the pressure of blood within the coronary vein to exceed its normal pressure during a portion of the cardiac cycle. This is illustrated in FIG. 9b wherein the normal pressure of blood within the coronary vein CV is illustrated by the dotted line, and wherein the modified pressure of blood within the coronary vein having the valving apparatus 110 of the present invention positioned therein is illustrated by the solid line. As shown, the valving apparatus 110 of the present invention serves to cause the pressure of blood within the coronary vein CV to raise to a substantially higher level (e.g., 40/hg) before the occluder flaps 114 of the valving apparatus 110 move to their open configuration, thereby allowing the pressure of blood within the coronary vein CV to once again fall.

It will be appreciated that the valving apparatus 110 of the present invention may optionally incorporate one or more of the following additional features:

The valving apparatus may be pucturable or traversable so as to permit a catheter to be passed through the valving apparatus in the event that such catheter passage becomes necessary at a later time;

The valving apparatus may be removable such that it may be rescued and removed from the body in the event it is no longer necessary, or if removal becomes desirable for some other reason;

The valving apparatus may be provided with projections, hooks, material for tissue in growth, or other suitable anchoring apparatus to assist in holding the valving apparatus in its desired position within the venus lumen; and The valving apparatus may be formed of radiologically imagable material, or may be provided with one or more radio dense or radio opaque markers to facilitate visualization of the valving apparatus by x-ray or fluoroscopy.

Figure 10:
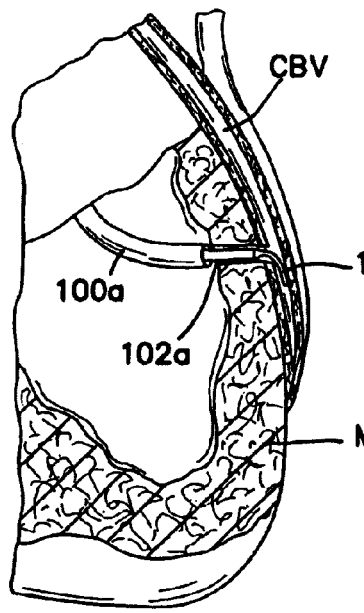
FIG. 10 is a partial longitudinal section view through a portion of a mammalian heart showing a passageway-forming catheter device of the present invention being used to form a transmyocardial passageway from a chamber of the heart, into a coronary blood vessel.

It is to be further appreciated that any of the transmyocardial passageways between a chamber of the heart and a coronary blood vessel CBV may be formed by any suitable means. In many instances, it will be desirable to pass a passageway-forming catheter 100 into one of the coronary blood vessels CBV and subsequently orienting the catheter such that the tissue-penetrating element of the catheter will pass from the coronary blood vessel CBV within which it is located into a chamber of the heart, such as the left ventricle. (see FIG. 11a) Alternatively, as shown in FIG. 10, a passageway-forming catheter 100a may be advanced into a chamber of the heart, such as the left ventricle LV, and will be oriented/positioned such that the tissue-penetrating element 102a of the catheter 100a is directed to the desired coronary blood vessel CBV. Thereafter, the tissue-penetrating element 102a is passed from the passageway-forming catheter 100a, through the wall of the myocardium M and into the desired coronary blood vessel CBV. A guidewire 104a may optionally be advanced through an optional lumen in the tissue-penetrating element 102a and into the coronary blood vessel CBV such that the tissue-penetrating element 102a may subsequently be retracted into the catheter 100a leaving the guidewire 104a extended through the transmyocardial passageway 10 and into the coronary blood vessel CBV. Thereafter, one or more passageway-modifying apparatus may be advanced over the guidewire 104a to modify or complete the formation of the desired transmyocardial passageway 10.

It will be appreciated that specific passageway-forming catheter devices 100, 100a, specific tissue-penetrating elements 102, 102a, and ancillary apparatus for modifying (e.g., sleeving, cauterizing, enlarging, stenting, valving, etc.) the transmyodardial passageway 10 have been fully described and claimed in earlier-filed applications of which this is a continuation-in-part.

The foregoing invention has been described hereabove with reference to certain presently preferred embodiments and examples only. No effort has been made to exhaustively describe all possible embodiments and examples in which the invention may be practiced. Indeed, various additions, deletions, modifications and alterations may be made to the above-described embodiments and examples without departing from the intended spirit and scope of the invention. Accordingly, it is intended that all such additions, deletions and modifications and alterations be included within the scope of the following claims.

What is claimed is:

1. A method for transmyocardial coronary revascularization, said method comprising the steps of:
   a) creating a bloodflow passageway that extends through myocardial tissue between a chamber of the heart and a coronary vein such that blood will flow from the chamber of the heart, through the bloodflow passageway and into the coronary vein; and
   b) causing the blood that flows from the chamber of the heart, through the bloodflow passageway and into the coronary vein to flow through the coronary vein in a direction opposite normal venous blood flow; and
   c) placing an intraluminal valving apparatus within the lumen of the coronary vein, said intraluminal valving apparatus having an opening through which blood emanating from the bloodflow passageway may flow and at least one occluder member that is alternately moveable between i) an open position whereby systolic blood is permitted to pass from the bloodflow passageway into the lumen of the coronary vein, and ii) a closed position whereby blood is prevented from backflowing from the lumen of the coronary vein into the bloodflow passageway.

2. The method of claim 1 wherein said coronary vein is situated next to a coronary artery, and wherein said method further comprises the step of:
   b) forming a fistulous connection between said coronary vein and said adjacent coronary artery, at a location which is downstream of said transmyocardial bloodflow passageway, such that blood may flow from the chamber of the heart, through said transmyocardial bloodflow passageway, through said vein, through said fistulous connection, and into the adjacent coronary artery so as to provide enhanced bloodflow through said coronary artery.

3. The method of claim 2 wherein said fistulous connection is a secondary bloodflow passageway which extends from said coronary vein to said coronary artery.

4. The method of claim 1 wherein Step b comprises blocking the lumen of the coronary vein at a location proximal to the location at which the bloodflow passageway enters the coronary vein, thereby causing the blood that enters the coronary vein from the blood flow passageway to flow through the coronary vein in a direction that is opposite normal venous blood flow.

5. The method of claim 4 wherein the lumen of the coronary vein is blocked by placing an embolic member within the lumen of the coronary vein.

6. The method of claim 4 wherein the lumen of the coronary vein is blocked by placing an intraluminal valving apparatus within the lumen of the coronary vein said intraluminal valving apparatus being alternately disposed in i) an open configuration which allows blood to flow through the lumen of the coronary vein in the direction of normal venous blood flow and ii) a closed configuration which prevents blood from flowing through the lumen of the coronary vein in the direction of normal venous bloodflow, said intraluminal valving apparatus being constructed to remain in its closed configuration until the pressure of blood within the lumen of the coronary vein distal to the intraluminal valving apparatus exceeds a predetermined maximum pressure, at which time the intraluminal valving apparatus will transition to its open configuration.

7. The method of claim 1 further comprising the step of: connecting an elastic closure member to cardiac tissue on either side of said transmyocardial bloodflow passageway, said elastic closure member being alternately transitionable between:
   i) a stretched configuration whereby said transmyocardial bloodflow passageway is opened to permit blood to flow from said fransmyocardial bloodflow passageway into said coronary vein; and
   ii) a retracted configuration whereby said fransmyocardial bloodflow passageway is substantially blocked so as to prevent blood from backflowing from said coronary vein into said transmyocardial bloodflow passageway.

8. The method of claim 1 further comprising the step of:
   b) placing an intracardiac valving apparatus within the chamber of the heart, adjacent one end of said transmyocardial bloodflow passageway, said intracardiac valving apparatus being alternately deployable in:
   i) an open position whereby bloodflow is permitted to pass through the transmyocardial bloodflow passageway in a first direction; and,
   ii) a closed position whereby blood is prevented from backflowing through the transmyocardial bloodflow passageway, in a second direction, said second direction being opposite said-first direction.

9. The method of claim 1 further comprising the step of:
   c) forming an endogenous tissue valve which is alternately moveable between:
   i) an open position whereby bloodflow is permitted to pass from said transmyocardial bloodflow passageway and through the lumen of said coronary vein, in a perfusion direction; and,
   ii) a closed position whereby said tissue valve will prevent blood from flowing from the coronary vein into said transmyocardial bloodflow passageway, in a backflow direction.

10. The method of claim 1 further comprising the step of:
    c) forming an endogenous tissue valve which is alternately moveable between:
    i) an open position whereby bloodflow is permitted to pass from said transmyocardial bloodflow passageway and through the lumen of said coronary vein, in a perfusion direction; and,
    ii) a closed position whereby said tissue valve will prevent blood from flowing from the coronary vein into said transmyocardial bloodflow passageway, in a backflow direction.

11. The method of claim 10 wherein said tissue valve is formed at the junction of the transmyocardial bloodflow passageway and the coronary vein.

12. The method of claim 11 wherein the tissue valve comprises at least one segment of the coronary vein in combination with at least one underlying segment of myocardial tissue.

13. The method of claim 12 wherein at least one segment of coronary vein and the at least one segment of underlying tapered segment of myocardial tissue which form said tissue valve are sized and configured such that, when systolic blood pressure is created within said transmyocardial bloodflow passageway, said tissue valve will move to its open position, and thereafter when diasfcolic blood pressure is present in said transmyocardial bloodflow passageway, said tissue valve will move to its closed position.

14. The method of claim 1 further comprising the step of:
connecting an elastic closure member to cardiac tissue on either side of said transmyocardial bloodflow passageway, said elastic closure member being alternately transitionable between:
i) a stretched configuration whereby said transmyocardial bloodflow passageway is opened to permit blood to flow from said transmyocardial bloodflow passageway into said coronary vein; and
ii) a retracted configuration whereby said transmyocardial bloodflow passageway is substantially blocked so as to prevent blood from backflowing from said coronary vein into said transmyocardial bloodflow passageway.

15. The method of claim 12 wherein said elastic closure member comprises a suture which is formed of elastic material, said suture being threaded through said myocardial tissue on opposite sides of said transmyocardial bloodflow passageway.

16. The method of claim 12 wherein said elastic closure member comprises a suture which is formed of elastic material, said suture being threaded through said myocardial tissue on opposite sides of said transmyocardial bloodflow passageway.

17. The method of claim 1 further comprising the step of:
b) placing an intracardiac valving apparatus within the chamber of the heart, adjacent one end of said transmyocardial bloodflow passageway, said intracardiac valving apparatus being alternately deployable in:
i) an open position whereby bloodflow is permitted to pass through the transmyocardial bloodflow passageway in a first direction; and,
ii) a closed position whereby blood is prevented from backflowing through the transmyocardial bloodflow passageway, in a second direction, said second direction being opposite said first direction.

18. The method of claim 17 wherein said transmyocardial bloodflow passageway is intended to provide a flow of blood from the chamber of the heart to the coronary vein, and wherein said first direction is the direction extending from the chamber of the heart to the coronary vein, and said second direction is the direction extending from the coronary vein to the chamber of the heart.

19. The method in claim 17 wherein said transmyocardial bloodflow passageway
is intended to drain blood from the coronary vein into the chamber of the heart, and wherein said first direction is the direction extending from the coronary vein to the chamber of the heart, and said second direction is the direction extending from the chamber of the heart to the coronary vein.

20. The method of claim 17 wherein the intracardiac valving apparatus provided in step b is attached to the wall of the chamber of the heart, and is positioned over the opening formed in the chamber of the heart by said transmyocardial bloodflow passageway.

21. The method of claim 20 wherein said intracardiac valving apparatus is sutured to the wall of the chamber of the heart.

22. The method of claim 20 wherein said intracardiac valving apparatus is adhered to the wall of the chamber of the heart.

23. The method of claim 1 further comprising the step of:
b) placing a protrusive stent within said transmyocardial passageway, such that said protrusive stent extends into said coronary vein.

24. The method of claim 23 wherein said protrusive stent is uncovered.

25. The method of claim 23 wherein said protrusive stent is at least partially covered.

26. The method of claim 23 wherein said protrusive stent incorporates at least one valve to intermittently block blood flow, in at least one direction, through said transmyocardial passageway.

27. The method of claim 1 wherein the intraluminal valving apparatus has a generally cylindrical body and an axial bore which extends longitudinally therethrough and wherein said at least one occluder member is positioned within said axial bore.

28. The method of claim 27 wherein the opening through which blood emanating from the bloodflow passageway may flow comprises a side aperture formed in the generally cylindrical body of said intraluminal valving apparatus, and wherein said side aperture is alienable with the bloodflow passageway such that blood from the bloodflow passageway may flow through said side aperture and into the axial bore of the intraluminal valving apparatus.

29. The method of claim 28 wherein said at least one occluder member is configured to close off said side aperture when in its closed position, such that a subsequent increase in blood pressure within the bloodflow passageway will move said occluder member to said open position, thereby reopening said side aperture.

30. The method of claim 29 wherein said at least one occluder member is positioned within the axial bore of the intraluminal valving apparatus such that during systole, bloodflow which passes from the bloodflow passageway into the axial bore of the intraluminal valving apparatus will force the occluder member to its open position thereby allowing bloodflow from the bloodflow passageway into the lumen of the coronary vein and, thereafter, during diastole, the occluder member will move to its closed position, thereby preventing blood from backflowing from the lumen of the coronary vein into the bloodflow passageway.

31. The method of claim 28 wherein the intraluminal valving apparatus further comprises a blocking member which closes off the axial bore of the intraluminal valving apparatus proximal to said side aperture.

32. The method claim 28 wherein the intraluminal valving apparatus further comprises a secondary occluder member that closes off the axial bore of the intraluminal valving apparatus proximal to the side aperture.

33. The method of claim 1 wherein the intraluminal valving apparatus is positioned within the coronary vein at a location distal to the location at which the bloodflow passageway enters the coronary vein, and wherein said at least one occluder member permits blood to flow through the lumen of the coronary vein in a direction opposite normal venous flow when said at least one occluder member is in its open position, and to prevent blood from backflowing through the coronary vein in the direction of normal venous flow when said at least one occluder member is in its closed position.

34. The method of claim 1 wherein two of said intraluminal valving apparatus are positioned in the lumen of the coronary vein, one of said valving apparatus being located proximal to the location at which the bloodflow passageway enters the coronary vein and the other of said valving apparatus being positioned distal to the location at which the bloodflow passageway enters the coronary vein.

* * * * *